US011626197B2

(12) United States Patent
Tabakin

(10) Patent No.: US 11,626,197 B2
(45) Date of Patent: Apr. 11, 2023

(54) SYSTEM AND PROCESS FOR MONITORING MEDICATION DOSAGE

(71) Applicant: MEDSENSE HEALTH, INC., Seattle, WA (US)

(72) Inventor: Matthew Blaine Tabakin, Seattle, WA (US)

(73) Assignee: MEDSENSE HEALTH, INC., Seattle, WA (US)

( * ) Notice: Subject to any disclaimer, the term of this patent is extended or adjusted under 35 U.S.C. 154(b) by 100 days.

(21) Appl. No.: 16/018,495

(22) Filed: Jun. 26, 2018

(65) Prior Publication Data

US 2019/0392934 A1    Dec. 26, 2019

(51) Int. Cl.
*G16H 20/10* (2018.01)
*G16H 10/60* (2018.01)
*G16H 80/00* (2018.01)

(52) U.S. Cl.
CPC ............. *G16H 20/10* (2018.01); *G16H 10/60* (2018.01); *G16H 80/00* (2018.01); *A61J 2200/30* (2013.01)

(58) Field of Classification Search
CPC ........ G16H 20/10; G16H 10/60; G16H 80/00; A61J 2200/30
See application file for complete search history.

(56) References Cited

U.S. PATENT DOCUMENTS

| 5,646,912 A | 7/1997 | Cousin |
| 6,604,650 B2 | 8/2003 | Sager |
| 7,715,277 B2 | 5/2010 | de la Huerga |
| 7,801,745 B2 | 9/2010 | Walker et al. |
| 7,844,361 B2 | 11/2010 | Jean-Pierre |
| 8,708,192 B2 | 4/2014 | Flowers et al. |
| 9,445,972 B2 | 9/2016 | Arad et al. |
| 9,474,695 B1 | 10/2016 | Khalid |
| 9,710,608 B2 | 7/2017 | Mikhail |
| 9,775,780 B2 | 10/2017 | Afsarifard et al. |
| 2003/0086338 A1 | 5/2003 | Sastry et al. |
| 2007/0097792 A1 | 5/2007 | Burrows et al. |

(Continued)

OTHER PUBLICATIONS

De Bleser et al. "How Accurate Are Electronic Monitoring Devices? A Laboratory Study Testing Two Devices to Measure Medication Adherence" Sensors ISSN 1424-8220. Mar. 2, 2010, pp. 1653-1660, https://www.researchgate.net/publication/221796079.

(Continued)

*Primary Examiner* — Sheetal R Paulson
(74) *Attorney, Agent, or Firm* — Husch Blackwell LLP

(57) ABSTRACT

The present disclosure provides a system. In an embodiment, a system for medication management is provided and includes a mobile device. The mobile device includes a dose software application (dose-app) configured to notify a user to take a medication from a medication container. The system also includes a motion detection component attached to the medication container. The motion detection component includes a motion detection device configured to detect container motion data and wirelessly transmit the motion data to the mobile device. The mobile device includes a wireless receiver configured to receive the motion data from the motion detection device and send the motion data to the dose-app. The dose-app is configured to determine whether the received motion data constitutes a valid medication dosage.

20 Claims, 19 Drawing Sheets

(56) References Cited

U.S. PATENT DOCUMENTS

| | | |
|---|---|---|
| 2016/0048657 A1 | 2/2016 | LeBrun et al. |
| 2016/0212389 A1 | 7/2016 | Mehrotra et al. |
| 2016/0239635 A1* | 8/2016 | Fateh .................. A61M 15/008 |
| 2017/0119628 A1 | 5/2017 | Geboers |
| 2017/0147786 A1 | 5/2017 | Rothschild |
| 2017/0296436 A1* | 10/2017 | Ziv ........................ G16H 20/10 |
| 2018/0028410 A1* | 2/2018 | Yun ........................ G08B 13/08 |
| 2018/0228696 A1* | 8/2018 | Rawal ..................... A61J 7/049 |
| 2018/0263854 A1* | 9/2018 | Taylor .................... B65D 41/04 |

OTHER PUBLICATIONS

"List of Adherence Aids" List compiled Mar. 26, 2013.
MEMS® 6 Medication Event Monitoring System. MEMS® 6 TrackCap CR (Article nr. 1021-01), 2002.
Shellmer et al. "The challenges of using medication event monitoring technology with pediatric transplant patients" NIH Public Access Author Manuscript, Pediatr Transplant. Jun. 2007; 11(4): pp. 422-428.
Kolandaivelu et al. "Non-adherence to cardiovascular medications" European Heart Journal (2014) 35, pp. 3267-3276.
"MEMS digital output motion sensor: ultra-low-power high-performance 3-axis "nano" accelerometer" STMicroelectronics, Datasheet—production data DocID17530 Rev 2, Dec. 2016, pp. 1-54.
Nordic Semiconductor, nRF51822. http://www.nordicsemi.com/eng/Products/Bluetooth-low-energy/nRF51822 pp. 1-3.
MEMS® Cap versatile adherence monitoring cap. http://www.medamigo.com/products/mems-cap. pp. 1-3.

* cited by examiner

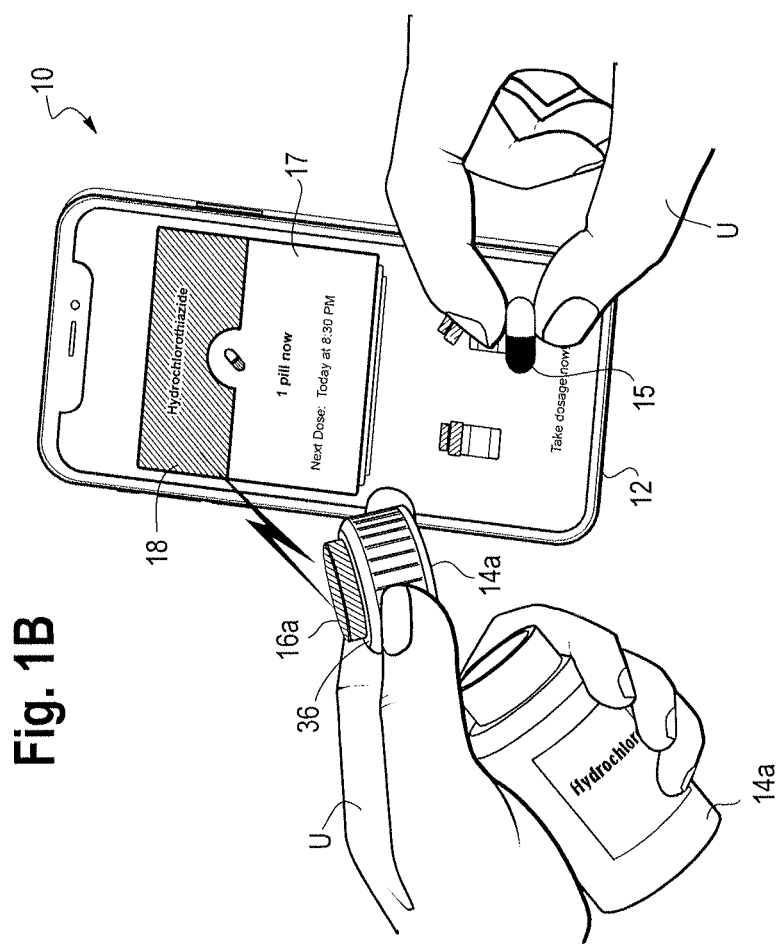

SYSTEM AND PROCESS FOR MONITORING MEDICATION DOSAGE

BACKGROUND

The present disclosure is directed to a system for monitoring medication dosage compliance, and specifically relates to a medication container with an attachable wireless motion detection component for active monitoring using a dose-application software on a mobile device.

Adherence to medication therapy is often a critical aspect of medical treatment, especially for the treatment of chronic conditions. In a recent survey, the number-one complaint by physicians is that patients do not follow treatment recommendations. The number of patients who do not take medications prescribed to them has reached epidemic proportions. Doctors' inability to provide optimal care as a result has mushroomed into one of the most pressing problems in healthcare today. In the United States alone, some 3.8 billion prescriptions are written every year, yet over 50% of them are taken incorrectly or not at all. As former Surgeon General C. Everett Koop aptly stated, "Drugs don't work in people who don't take them."

The thousands of medical studies conducted on the topic of patient adherence to medication therapy, consistently rank patient forgetfulness as the number-one barrier to medication compliance. One conventional approach to improving patient adherence is electronic monitoring. Electronic Monitoring (or "EM") is oftentimes referred to as the "gold standard" for generating information regarding the taking and the timing of drug intake by a patient. A known EM device is the Medication Event Monitoring System (or "MEMS") from Aardex, Switzerland. The MEMS consists of a pill bottle fitted with a cap, containing a microelectronic circuit, that registers the date and time of opening of the bottle. However, the MEMS has several drawbacks. First, use of the MEMS requires the patient to transfer the medications from the originally prescribed medication container into the MEMS container. Second, MEMS is ineffective for medications that cannot be transferred to the MEMS container such as blister pack medications, inhaler-type medications, liquid medications, and/or medications stored in a tube. Third, MEMS does not differentiate one medication from the other. Finally, the MEMS system does not remind a patient which medication to take, when to take the medication, and the proper dosage at the time of ingestion.

Consequently, the art recognizes the need for a medication dosage and monitoring system that is convenient and is user-friendly so as to promote and improve the user's compliance with a medication dosage protocol. A need further exists for a medication management and monitoring system that can be used with the original medication container.

SUMMARY

The present disclosure provides a system. In an embodiment, a system for medication management is provided and includes a mobile device. The mobile device includes a dose software application (dose-app) configured to notify a user to take a medication from a medication container. The system also includes a motion detection component attached to the medication container. The motion detection component includes a motion detection device configured to detect container motion data and wirelessly transmit the motion data to the mobile device. The mobile device includes a wireless receiver configured to receive the motion data from the motion detection device and send the motion data to the dose-app. The dose-app is configured to determine whether the received motion data constitutes a valid medication dosage.

The present disclosure provides a process. In an embodiment, a process for managing medication is provided and includes synchronizing a motion detection component with a dose software application (dose-app) on a mobile device. The motion detection component is attached to a medication container. The dose-app is embodied in instructions stored by the mobile device that, when executed by the mobile device, the dose-app is configured to send a notification to a user to take a medication from the medication container. The dose-app is also configured to wirelessly receive motion data from the motion detection component. The dose-app is also configured to determine whether the motion data constitutes a valid medication dose.

BRIEF DESCRIPTION OF THE DRAWINGS

The accompanying Figures together with the following description serve to illustrate and provide a further understanding of the disclosure and its embodiments and are incorporated in and constitute a part of this specification.

FIG. 1B is a perspective view of the motion detection component transmitting motion data to the dose-app during a medication dosage event, in accordance with an embodiment of the present disclosure.

DEFINITIONS

Figure 1A:
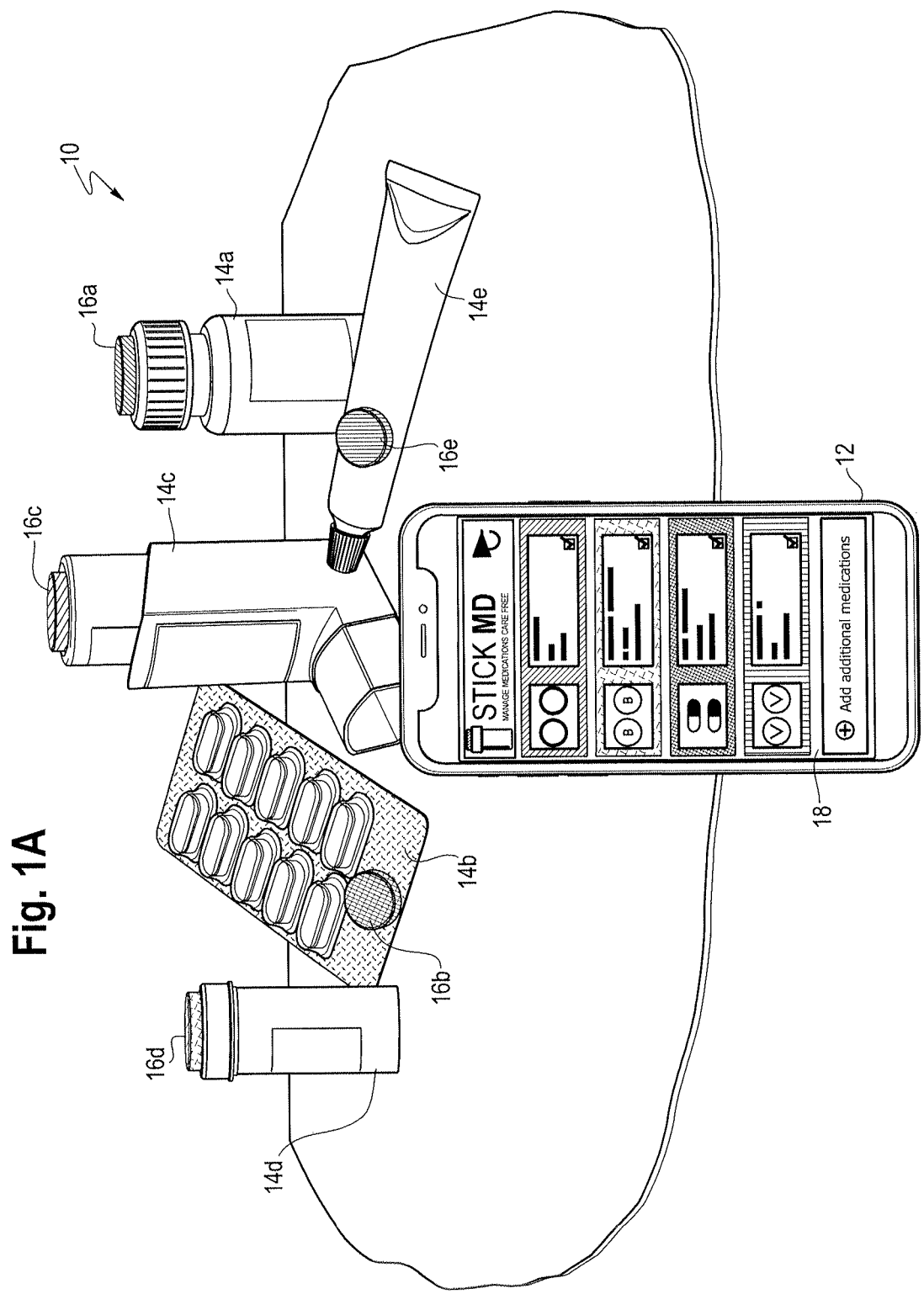
FIG. 1A is a perspective view of a system for medication management having a mobile device with a dose application software (dose-app) and a plurality of medication containers, each medication container with a respective motion detection component attached thereto, in accordance with an embodiment of the present disclosure.

An "access point," or ("AP") in computer networking, or a wireless access point (WAP), is a networking hardware device that allows a Wi-Fi device to connect to a wired network. The AP usually connects to a router (via a wired network) as a standalone device, but it can also be an integral component of the router itself. An AP is differentiated from a hotspot, which is the physical location where Wi-Fi access to a WLAN is available.

"Application software" (an "application" or an "app") is a set of computer programs designed to permit the user to perform a group of coordinated functions, tasks, or activities. Application software cannot run on itself but is dependent on system software to execute. A mobile application (or "mobile app") is application software developed specifically for use on small, wireless computing devices, such as smartphones, tablets, and mobile devices, rather than desktop computers or laptop computers.

The term "communicates" or "in communication with" or "communicatively connected," "communicatively linked" and like terms denotes a link between two or more objects (i.e., a link between two or more modules, units, sub-units, computing devices, processors, servers, etc.) that enables two-way exchange of information and includes a wired connection, a wireless connection, and combinations thereof.

The terms "comprising," "including," "having," and their derivatives, are not intended to exclude the presence of any additional element, component, step or procedure, whether or not the same is specifically disclosed. In contrast, the term, "consisting essentially of" excludes from the scope of any succeeding recitation any other element, component, step or procedure, excepting those that are not essential to operability. The term "consisting of" excludes any element, component, step, or procedure not specifically delineated or listed.

A "computing device" (or "a computer readable device") is a non-transitory computing device with a central processing unit (CPU), random access memory (RAM), and a storage medium (such as hard disk drive, solid state drive, flash memory, and cloud storage). Nonlimiting examples of computing devices include personal computers (PCs), smart phones, laptops, mobile devices, tablet PCs, and servers. The term "computing device" may also describe two or more computing devices communicatively linked in a manner as to distribute and share one or more resources, such as clustered computing devices and server banks/farms. It is understood that any number of computing devices could be used, and embodiments of the present disclosure are contemplated for use with any computing device.

The "Internet" refers to interconnected (public and/or private) networks that may be linked together by protocols (such as TCP/IP and HTTP) to form a globally accessible distributed network. While the term Internet refers to what is currently known (e.g., a publicly accessible distributed network), it also encompasses variations which may be made in the future, including new protocols or any changes or additions to existing protocols.

A "mobile application," (or "mobile app"), is a type of software application designed to run on a mobile device, such as a smartphone or a tablet computer. Mobile applications frequently serve to provide users with similar services to those accessed on PCs. Mobile apps are generally small, individual software units with limited function. Mobile apps typically are Internet applications that run on smartphones, computer tablets (such as iPad available from Apple, or Surface available from Microsoft). Some mobile apps take personal computer (PC)-based applications and port them to a mobile device.

A "local area" is defined as the wireless communication transmitting range for the motion detection component. In an embodiment, the local area is defined by the transmitting range for a Bluetooth device (in the motion detection component), which is presently from 1 meter (m), or 5 m, or 10 m to 20 m, or 50 m, or 75 m, or 100 m. It is understood that improvements in Bluetooth technology may extend the wireless communication transmission range thereby expanding the area for the local area.

A "mobile device" is a portable, wireless computing device that is small enough to be used while held in the hand; a hand-held device. A mobile device typically has a user interface display screen with touch input and/or a miniature keyboard and weighs less than 0.91 kilograms (kg) (2 pounds). A mobile device typically has an operating system (OS) and can run various types of application software (apps). Nonlimiting examples of a mobile device include smartphone, personal digital assistant (PDA), tablet computer and wireless wearable technology such as a smartwatch or Apple watch, for example.

A "serial peripheral interface" (or "SPI") is an interface bus commonly used to send data between microcontrollers and small peripherals devices such as shift registers, sensors, and SD cards. It uses separate clock and data lines, along with a select line for communicating with a desired peripheral device. The SPI bus (cAPTAIN) is a synchronous serial communication interface specification used for short distance communication, primarily in embedded systems. The interface was developed by Motorola in the mid 1980s and has become a de facto standard. Typical applications include Secure Digital ("SD") cards and liquid crystal displays. SPI devices communicate in full duplex mode using a master-slave architecture with a single master. The master device originates the frame for reading and writing. Multiple slave devices are supported through selection with individual slave select (SS) lines. Sometimes SPI is called a four-wire serial bus, contrasting with three-, two-, and one-wire serial buses. The SPI may be accurately described as a synchronous serial interface, but it is different from the synchronous serial interface (SSI) protocol, which is also a four-wire synchronous serial communication protocol. SSI Protocol employs differential signaling and provides only a single simplex communication channel.

A "server" is a computer program that provides services to other computer programs (and their users) in the same or other computing devices. The computing device that a server program runs in is also frequently referred to as a server (though it may be used for other purposes as well). In the client/server programming model, a server is a program that awaits and fulfills requests from client programs in the same or other computing devices. A given application in a computing device may function as a client with requests for services from other programs and also as a server of requests from other programs. Specific to the Web, a Web server is the computer program (housed in a computing device) that serves requested HTML pages or files. A Web client is the requesting program associated with the user. For example, the Web browser in a home PC is a client that requests HTML files from a Web server.

"Transmission Control Protocol" or ("TCP") is one of the main protocols of the Internet protocol suite. It originated in the initial network implementation in which it complemented the Internet Protocol (IP). Therefore, the entire suite is commonly referred to as TCP/IP. TCP provides reliable, ordered, and error-checked delivery of a stream of octets (bytes) between applications running on hosts communicating via an IP network. Major Internet applications such as the World Wide Web, email, remote administration, and file transfer rely on TCP. Applications that do not require reliable data stream service may use the User Datagram Protocol (UDP), which provides a connectionless datagram service that emphasizes reduced latency over reliability.

A "Uniform Resource Locator" (or "URL") is a formatted text string used by Web browsers, email clients, software, and apps to identify a network resource on the Internet. Network resources are files that can be plain Web pages, other text documents, graphics, or programs. A URL typically includes three subcomponents: (1) a network protocol, (2) a host name or address, and (3) a file or resource location.

A "user" of the present system is (i) a person targeted to ingest the medication (i.e. the patient), (ii) a caretaker of the patient (family member, friend, healthcare provider), and (iii) a combination of (i) and (ii).

"Wireless communication" refers to a network of terminals that uses electromagnetic waves (including RF, IR, Laser, visible light and acoustic energy) rather than wire conductors for telecommunications. This electromagnetic spectrum is a range of frequencies from zero to infinity. However, this spectrum by custom and practice was formerly divided into 26 alphabetically designated bands. This usage still prevails to some degree but has a frequency of 30 Hz to 3000 GHz. Wireless telephone technology includes cell phones, pagers, GPS, cordless computer peripherals, cordless telephone sets, home entertainment system control boxes, remote controls, two way radios, baby monitors, satellite television and wireless LANs. Other wireless communication includes GSM, GPRS, EDGE, UMTS, WAP, iMODE, TDMA, CDMA, PCS, etc. Wireless communication also includes technologies such as Near Field Communications (NFC), Wi-Fi, infrared, Bluetooth, and Bluetooth Low Energy. "Bluetooth" communication is an open wireless technology standard for transmitting fixed and mobile electronic device data over short distances. Bluetooth wireless communication communicates with a variety of electronic devices and creates personal networks operating within the unlicensed 2.4 GHz band. Operating range is based on device class. A variety of digital devices use Bluetooth communication, including MP3 players, mobile devices, peripheral devices and personal computers.

A "web site" refers to a system that serves content over a network using the protocols of the World Wide Web. A web site may correspond to an Internet domain name, and may serve content associated or provided by an organization. The term may encompass (i) the hardware/software server components that serve objects and/or content over a network, and/or (ii) the "backend" hardware/software components, including any standard, non-standard or specialized components, that may interact with the server components that provide services for Web site users.

The "World Wide Web" (or "Web") refers to (i) a distributed collection of user-viewable or accessible documents (that may be referred to as Web documents or Web pages) or objects that may be accessible via a publicly accessible distributed network like the Internet, and/or (ii) the client and server software components which provide user access to documents and objects using communication protocols. A protocol that may be used to locate, deliver, or acquire Web documents or objects through HTTP (or other protocols), and the Web pages may be encoded using HTML, tags, and/or scripts. The terms "Web" and "World Wide Web" encompass other languages and transport protocols including or in addition to HTML and HTTP that may include security features, server-side, and/or client-side scripting.

The numerical ranges disclosed herein include all values from, and including, the lower value and the upper value. For ranges containing explicit values (e.g., a range from 1 or 2, or 3 to 5, or 6, or 7) any subrange between any two explicit values is included (e.g., the range 1-7 above includes subranges, 1 to 2; 2 to 6; 5 to 7; 3 to 7; 5 to 6; etc.).

DETAILED DESCRIPTION

The present disclosure provides a system. In an embodiment, a system for medication management is provided and includes a mobile device, a medication container, and a motion detection component. The mobile device includes a dose software application (hereafter interchangeably referred to as "dose-app"). The motion detection component is attached to the medication container. The motion detection component includes a motion detection device. The motion detection device is configured to detect container motion data and wirelessly transmit the motion data to the mobile device. The dose-app is configured to notify a user to take a medication from a medication container. The mobile device includes a wireless receiver configured to receive the motion data from the motion detection device and send the motion data to the dose-app. The dose-app is configured to determine whether the received motion data constitutes a valid medication dosage.

FIG. 1A is a perspective view of a system 10 for medication management. System 10 also monitors medication dosage and compliance. The system 10 includes a mobile device 12, one or more a medication containers 14a, 14b, 14c, 14d, and 14e, and a motion detection component for each respective medication container, motion detection components 16a, 16b, 16c, 16d, and 16e. Each motion detection component 16a, 16b, 16c, 16d, and 16e is attached to a respective medication container 14a, 14b, 14c, 14d, and 14e. Although FIG. 1A shows system 10 with five medication containers (and five corresponding motion detection components), it is understood that the system 10 may include one, or two, or three, or four to five, or six, or seven, or eight, or nine, or 10, or more medication containers (and corresponding same number of motion detection components).

The mobile device 12 includes a dose software application 18 (hereafter interchangeably referred to as a "dose-app"). The dose-app 18 is embodied in instructions on the mobile device 12 and the dose-app 18 is configured to interact with (and communicate with) the motion detection component 16 and perform other functions as will be explained in detail below.

1. Medication Container

The system 10 includes a medication container. The medication container stores, holds, or otherwise contains a medication. The system 10 advantageously operates with a wide variety of medication containers and medications. The medication can be a solid, a liquid or a gas with the medication container taking suitable structure and shape to appropriately store the medication. Nonlimiting examples of suitable medication containers (with the form of the medication in parentheses) include pharmacy bottle with screw-on cap (for pills and/or liquid medication such as a syrup, for example); pharmacy bottle with flip-top cap (for pills and/or liquid medication); pill organizers with a flip-top cap (for pill and/or suppository medication); blister pack (for pill and/or suppository medication); a tube (for medication that is a suave, a balm, an oil, an ointment, a salve, a crème, or a gel); an inhaler (for medication that is a gas or an aerosol spray); a syringe pack (for medication that is an injection dose); a foil pouch (for medication that is a pill or suppository). Other nonlimiting examples of suitable medication containers include pharmacy vials, inhaler spacers, nebulizers, ampoules, pouches, medication tubes, and intravenous (IV) containers. An advantage of the present system is its versatility to operate effectively with myriad types of medication containers and medications, as set forth above.

A nonlimiting example of the present system is system 10 shown in FIG. 1A, whereby system 10 includes medication container 14a which is a screw cap bottle for holding pills, medication container 14b which is a blister pack for holding gel capsules, medication container 14c which is a gas inhaler for delivering an aerosol spray of medication, medication container 14d which is a pharmacy container (typically made of a translucent orange polymeric material) with a screw-on cap for holding pills, and medication container 14e which is a tube for delivering a medication that is a topical cream.

Although the following description is directed to a screw cap bottle (i.e., medication container 14a), it is understood that the present system 10 may be used with one or more of the foregoing medication containers and medications and that the following description to medication container 14a applies equally to medication containers 14b-14e.

2. Motion Detection Component

The present system includes one or more motion detection components (hereafter interchangeably referred to as "MDC"). Each medication container in the system has a corresponding MDC attached thereto. FIG. 1A shows an embodiment of the present system whereby system 10 includes MDCs 16a-16e that are attached to respective medication containers 14a-14e: MDC 16a is attached to medication container 14a, MDC 16b is attached to medication container 14b, MDC 16c is attached to medication container 14c, MDC 16d is attached to medication container 14d, and MDC 16e is attached to medication container 14e.

Although the following disclosure of the present system is directed medication container/MDC pair 14a/16a, it is understood the description to 14a/16a applies equally to the other medication container/MDC pairs: 14b/16b, 14c/16c, 14d/16d, and 14e/16e. FIG. 1B shows system 10 and the mobile device 12 displaying a notification 17 to a user. The notification 17 instructs the user U (hands of user shown) to take a medication 15 from medication container 14a. Simultaneously, MDC 16a is wirelessly transmitting motion data of the medication container 14a to the dose-app 18. Further operation of the system 10 will be discussed in detail below.

Figure 2B:
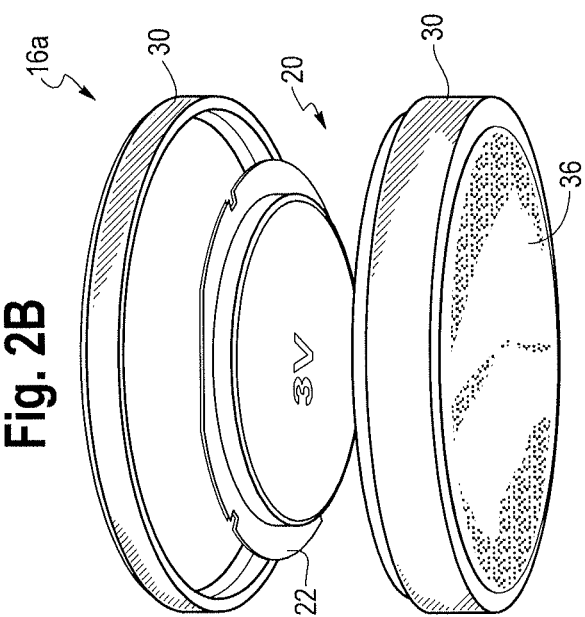
FIG. 2B is an exploded perspective view of the motion detection component of FIG. 2A, in accordance with an embodiment of the present disclosure.
Figure 3B:
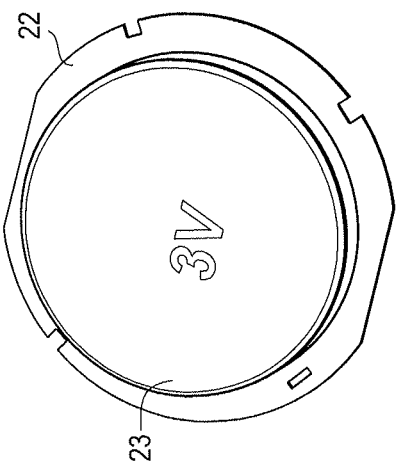
FIG. 3B is a bottom perspective view of the printed circuit board and a battery of the motion detection component of FIG. 2B, in accordance with an embodiment of the present disclosure.

As shown in FIGS. 2A, 2B, and 3A and 3B, the motion detection component 16a includes a battery 20, a printed circuit board (PCB) 22, a processor 24, a motion detection device 26, a wireless communication component (WCC), and a housing 30. The PCB 22 is located on a top surface of the battery 20, the PCB 22 having a first contact and a second contact (not shown) electrically connected to respective positive electrode and negative electrode of the battery 20. The battery 20 is electrically connected to the PCB 22. In an embodiment, the battery 20 is a button cell 23 as shown in FIGS. 2B-2C. A "button cell," as used herein, is a small single cell battery shaped as a squat cylinder typically from 5 millimeter (mm) to 25 mm in diameter and from 1 mm to 6 mm in height and resembles a button on a garment, hence the term "button cell." A metal can forms the bottom body and the positive electrode of the button cell. An insulated top metal cap forms a top surface of the button cell and is also the negative electrode of the button cell.

The button cell 23 provides from 3.0 volts to 3.7 volts. Nonlimiting examples of suitable button cells include lithium manganese dioxide ($LiMnO_2$) primary cells (CR type), lithium/carbon monofluoride Li-(CF) primary cells (BR type), and lithium polymer rechargeable cells.

In an embodiment, the button cell is a CR2032 micro lithium button cell available from Panasonic, Duracell, or Energizer.

The PCB 22 is located on a top surface of the button cell 23. The PCB 22 has a first contact and a second contact (not shown) electrically connected respectively to the positive electrode (metal can body) and the negative electrode (top cap) of the button cell 23.

The PCB 22 includes a processor 24 and a wireless communication component (hereafter "WCC") electrically connected to the PCB 22, or otherwise surface mounted onto the PCB 22. The processor and the WCC may be discrete components. Alternatively, the processor and the WCC may be subcomponents of an integrated component. It is understood that PCB 22 may include passive components as necessary to complete circuitry. Nonlimiting examples of passive components that may be present on the PCB 22 include resistor, capacitor, inductor and filters (SAW/BAW/Balun), and any combination thereof.

In an embodiment, the motion detection component 16a includes a system-on-chip module 32 (or "SoC 32") electrically connected to the PCB 22, or surface mounted on the PCB 22. A "SoC," as used herein, is an integrated circuit that integrates multiple components for a complete electronic system. The SoC 32 includes digital, analog, mixed-signal, and radio-frequency functions—all on a single substrate. The SoC 32 integrates the processor and the WCC into a single component. In other words, when SoC 32 is present, the processor 24 may or may not be necessary. The SoC 32 is built around a microprocessor with flash memory and random access memory (RAM). The SoC 32 also includes an antenna and a transceiver which supports near field wireless communication (such as Bluetooth or Bluetooth low energy wireless communication). The components are incorporated into the SoC 32 module in the form of discrete integrated devices. The SoC 32 may also include one or more analog or digital peripheral components.

In an embodiment, the SoC 32 is an nRF52832 multiprotocol SoC available from Nordic Semiconductor.

The motion detection component 16a includes a motion detection device 26, (hereafter interchangeably referred to as "MDD26," or "MDD") electrically connected to the PCB 22, or surface mounted on the PCB 22. A "motion detection device" as used herein, is a device that detects movement of an object upon which the motion detection device is attached. In other words, the motion detection device measures movement of the medication container upon which the motion detection device is attached. Nonlimiting examples of suitable motion detection devices include accelerometer, gyroscope, orientation sensor, and combinations thereof.

An "accelerometer" is a device that measures acceleration. An accelerometer measures changes in velocity and/or changes in position (by integrating the signal) in one, two, or three axes. Nonlimiting examples of suitable accelerators include Micro-Electro-Mechanical Systems (MEMS) accelerometer, piezo resistive accelerometer, low impedance output accelerometer, "high impedance" charge output accelerometer (type of piezoelectric), and triaxial accelerometer.

A "gyroscope" is a device that measures changes in orientation and/or changes in rotational velocity. In other words, "gyroscope" is a device that detects the angular velocity on all three axes. Nonlimiting examples of suitable gyroscopes include MEMS gyroscopes, solid-state ring laser gyroscopes, fiber optic gyroscopes, quantum gyroscopes, tuning work gyroscope, vibrating wheel gyroscope, hemispherical resonator gyroscope, and foucault pendulum gyroscope.

An "orientation sensor" is a device that measures azimuthal, pitch and the roll in degrees. The azimuthal is the angle between the longitudinal axis and the Earth's magnetic field. The pitch (angle between the plane parallel to the ground and the plane of the screw cap) pitch measures the "tilt" of an object, and the roll (the angle formed by tilting the device either left or right.

In an embodiment, the orientation sensor is a 9-axis absolute orientation sensor which is a combination of a 3-axis acceleration sensor, a 3-axis gyroscope and a 3-axis geomagnetic sensor. Nonlimiting examples of suitable 9-axis orientation sensors include the BMX160 orientation sensor and the BMX055 orientation sensor available from Bosch Sensortec.

In an embodiment, the motion detection device 26 is a three-axis accelerometer.

In an embodiment, the motion detection component 16a includes a memory chip 34 for storing motion data when the mobile device is out of the local area. The memory chip can be a non-volatile memory chip. A "non-volatile memory chip" is a memory chip that retains its data when its power supply is switched off and can retrieve the stored data after a power supply has been turned off and back on. Nonlimiting examples of suitable non-volatile memory chips include an erasable programmable read-only memory chip (EPROM) and an electrically erasable programmable read-only memory chip (EEPROM).

In an embodiment, the memory chip is an EEPROM chip. The EEPROM chip inside the motion detection component will save the accelerometer data and any other sensor specific data when the mobile device is out of the local area during a dosage. Medications that are taken "As Needed" for example, do not have reminder notifications associated therewith. However, the EEPROM chip is able to save motion data if a medication dosage occurs when the mobile device is outside the local area. The MDC can then upload the motion data stored in the EEPROM to the mobile device when the mobile device comes into the local area. When the mobile device is out of the local area and the user would like to take a medication dosage, the memory chip 34 enables the motion detection component 16a to store the data for the dosage event for later transmission to the dose-app 18.

3. Housing

Figure 2A:
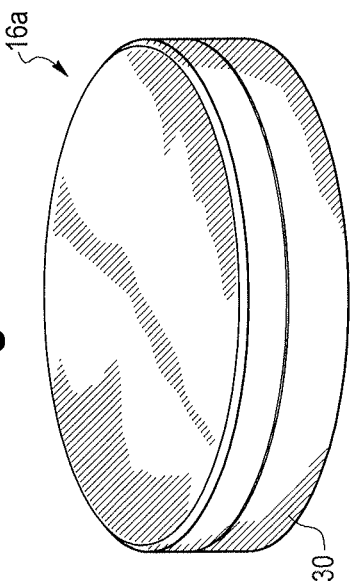
FIG. 2A is a perspective view of the motion detection component in accordance with an embodiment of the present disclosure.
Figure 3A:
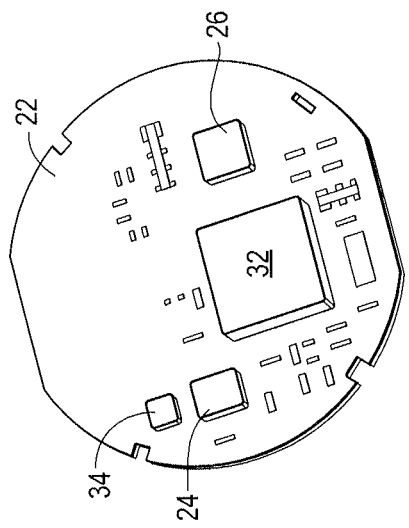
FIG. 3A is a top perspective view of a printed circuit board of the motion detection component of FIG. 2B, in accordance with an embodiment of the present disclosure.

The motion detection component 16a includes a housing 30. FIGS. 2A, 2B show the PCB 22 (with motion detection device 26, SoC 32 and other components mounted thereon) and button cell 23 enclosed within housing 30. The housing 30 encases the button cell 23, the PCB 22, with the aforementioned components surface mounted thereon. The housing 30 provides physical and mechanical protection to the button cell-PCB assembly. The housing 30 may or may not provide a water-proof barrier for the button cell-PCB-sensor module assembly.

Nonlimiting examples of suitable materials for the housing 30 include polymeric material, rubber (including silicone rubber), metal, wood, glass, and combinations thereof.

The housing 30 includes an indicium. When two or more MDCs are present, each MDC has a respective and distinct indicium to distinguish or otherwise identify one MDC from another MDC.

Nonlimiting examples of suitable indicium for the MDC includes text on the housing, color of the housing, shape of the housing, design/symbol on the housing (zig-zag, shapes, diagonal lines, etc.) and any combination thereof. In an embodiment, the user can purchase a kit with a plurality of MDCs for use with a plurality of respective medications/medication containers. Each MDC in the kit has a housing with a different color—a blue MDC, a red MDC, a green MDC, a yellow MDC, etc. In this way, the indicium is the color of the housing, the different housing colors distinguishing the MDCs from one another. The housing color can be matched with a respective medication/medication container as will be described in detail below.

Returning to FIG. 1A, system 10 shows an embodiment whereby the housing of MDC 16a is a first color, the housing of MDC 16b is a second color, the housing of MDC 16c is a third color, the housing of MDC 16d is a fourth color, and the housing of MDC 16e is a fifth color—each of the five colors different from one another. The five different housing colors are depicted by different hatching in FIG. 1A.

Returning to FIGS. 2A-3B, in an embodiment, the MDC 16a includes the button cell-PCB-sensor module assembly encased in the housing 30. The motion detection component 16a (with housing 30) has a length L from 10 mm, or 15 mm, or 20 mm to 25 mm, or 30 mm; a height H from 3 mm, or 4 mm, or 5 mm to 6 mm, or 7 mm, or 8 mm, or 9 mm, or 10 mm; and a width W from 10 mm, or 15 mm, or 20 mm to 25 mm, or 30 mm.

The motion detection component 16a (or "MDC") is attached to the medication container 14a. In an embodiment, the MDC 16a is releasably attached to the medication container 14a.

In an embodiment, the motion detection component 16a includes a strip of adhesive material 36 (FIGS. 1B, 2B) on one of the exterior surfaces of the housing 30. The strip of adhesive material releasably attaches the motion detection component 16a to the medication container 14a. An advantage of the present system is the ability to use and re-use the motion detection component with one or more different medication containers. Once a prescription has been fully consumed and the medication period has ended, the motion detection component may be removed from the empty or completed medication container. The user may re-program or otherwise re-synchronize the motion detection component with the dose-app 18 for use with another medication. The user can remove the motion detection component from the used container and releasably attach the reprogrammed motion detection component onto a second container, the second container storing a second medication. The previously-used MDC can be synchronized (or re-synchronized) for another medication vis-a-vis the dose-app 18. The second medication container may be the same or different than the first medication container.

The motion detection component 16a wirelessly communicates with the mobile device 12 and dose-app 18 as will be described below.

4. Enter Medication

Figure 4:
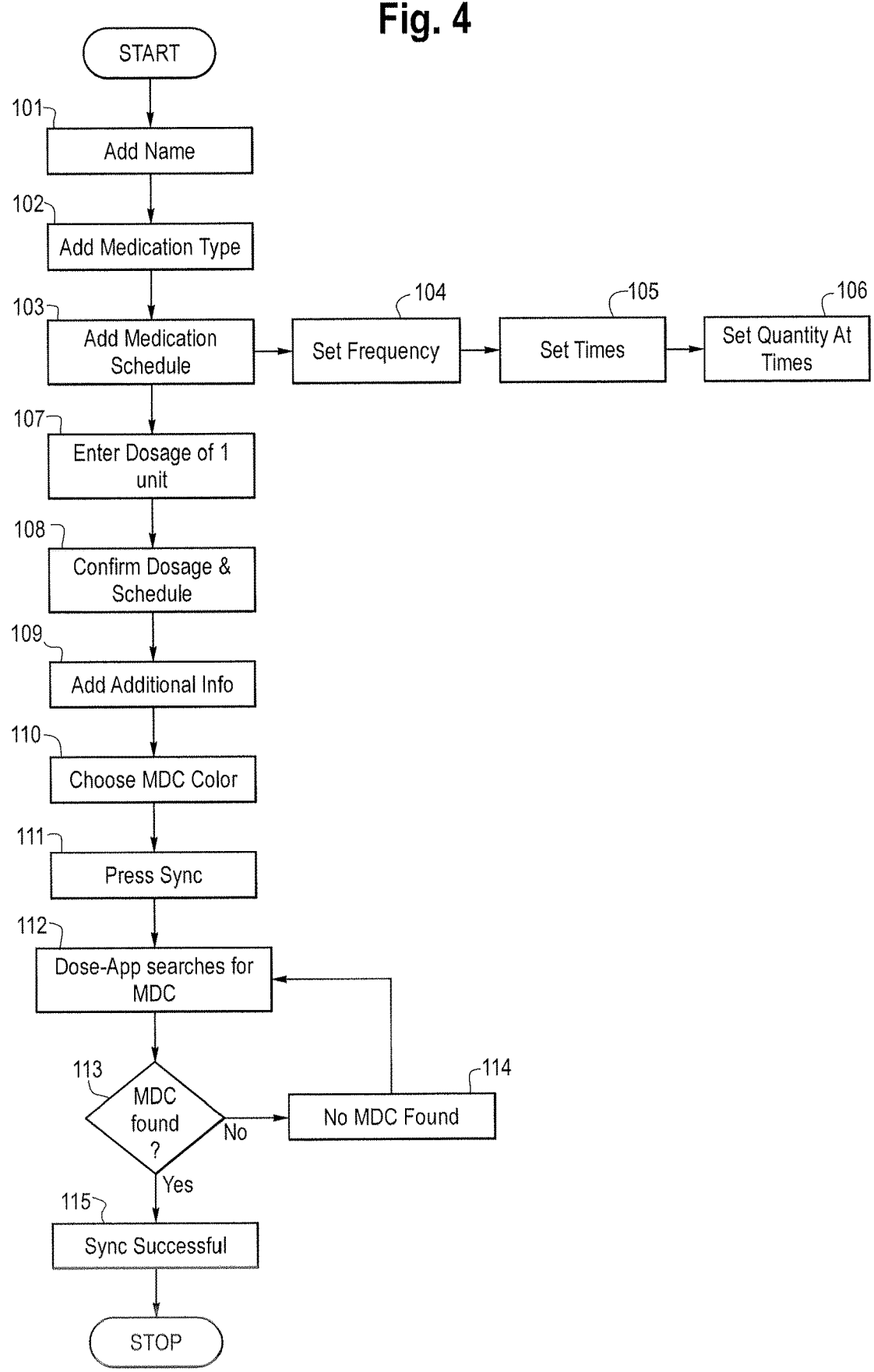
FIG. 4 is a flowchart illustrating a process for a user to enter medication information into the dose software application and synchronizing the dose application software in accordance with an embodiment of the present disclosure.

The dose-app 18 is a software application integrated into the mobile device 12. FIG. 4 shows the process by which a user inputs medication data into the dose-app 18. FIGS. 5-10 show display screens of the mobile device 12, the display screens of FIGS. 5-10 corresponding to the steps in the flowchart of FIG. 4.

Figure 5:
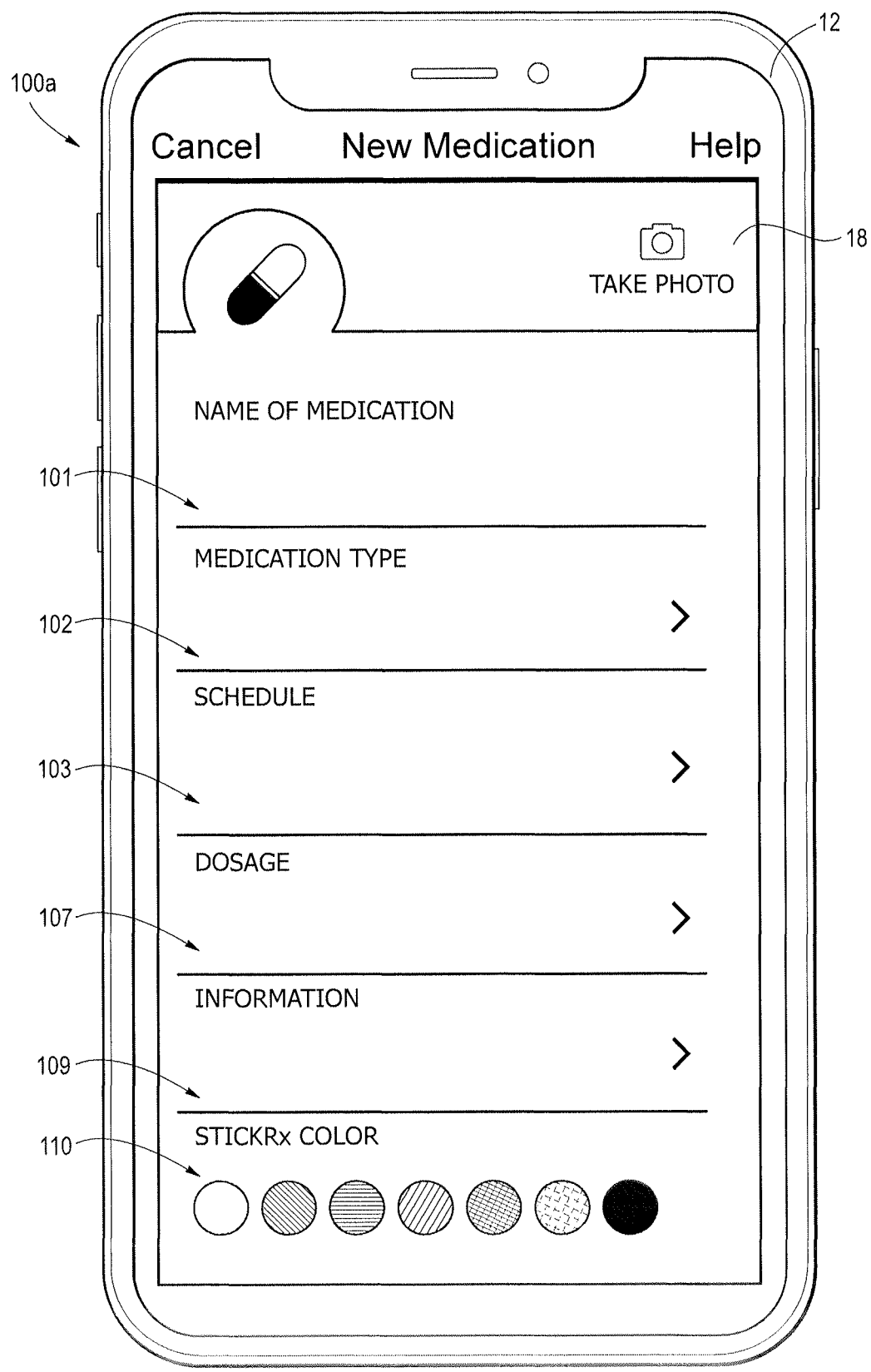
FIG. 5 is a front elevation view of a user input screen for new medication in accordance with an embodiment of the present disclosure.

FIG. 5 is a display screen 100a generated by the dose-app 18 which is displayed on mobile device 12. Screen 100a shows menu options whereby the user inputs, or otherwise enters, medication information such as Medication Name 101, Medication Type 102, Medication Schedule 103, Set Frequency 104, Set Times 105, Set Quantity at Times 106, Dosage 107, Confirm Dosage and Schedule 108, Additional Information 109, and Synchronization 110-111. Through one or more screens on the dose-app 18, the user inputs medication information, synchronizes the dose-app 18 with the MDC 16, and configures system 10 for operation.

As shown in the flowchart in FIG. 4, the user enters the name of the medication at step 101. For example, the user can enter the medication name "Hydrochlorothiazide" at 101 and screen 100b shown in FIG. 6. The term "input" or "enters," as used herein, can be one or more actions performed by the user: (i) a typed entry, (ii) a selection from a drop-down menu, and (iii) a combination of (i) and (ii). The user may be prompted to add a photo of the medication, if desired.

Figure 6:
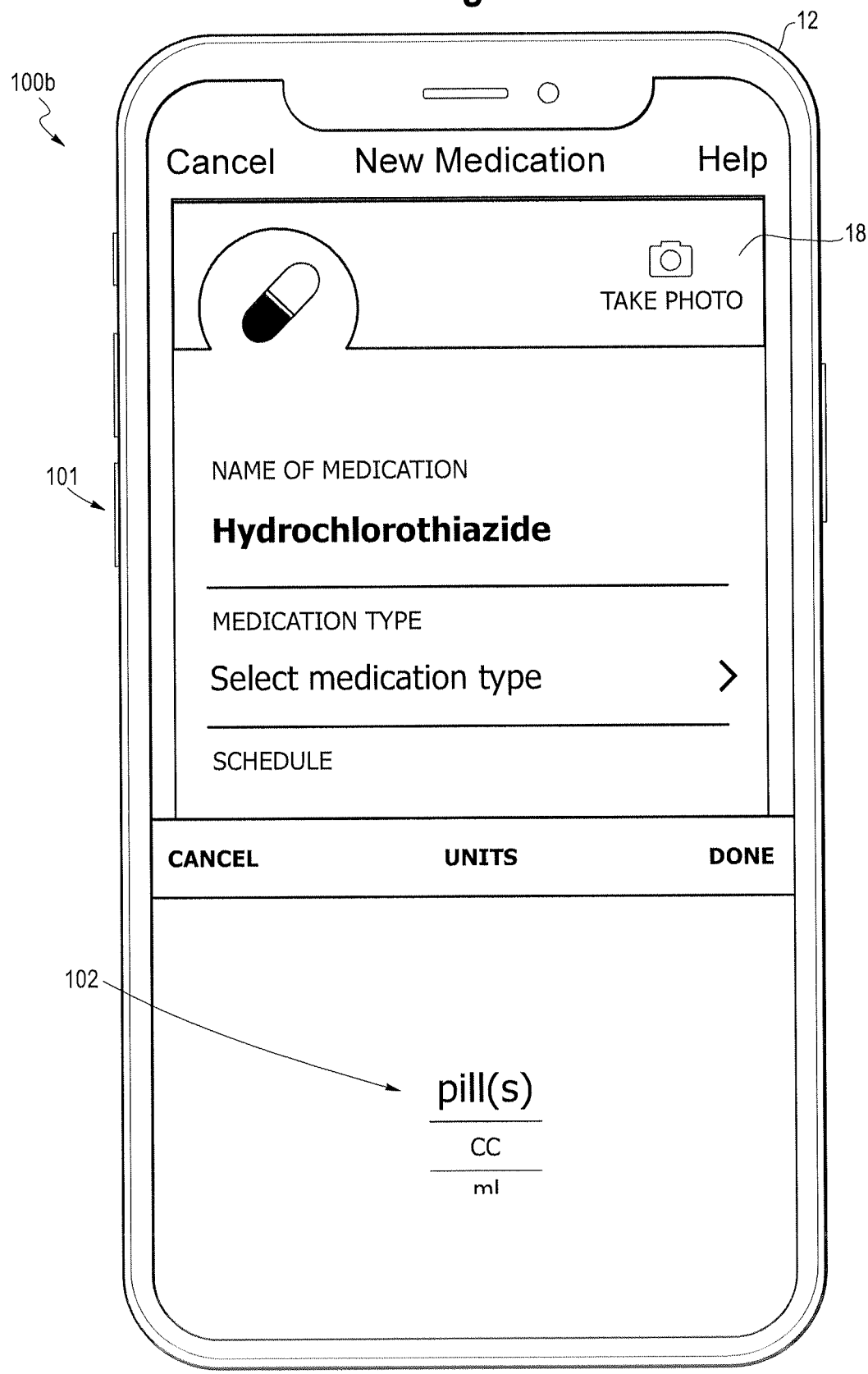
FIG. 6 is a front elevation view of a user input screen for name of medication in accordance with an embodiment of the present disclosure.
Figure 7:
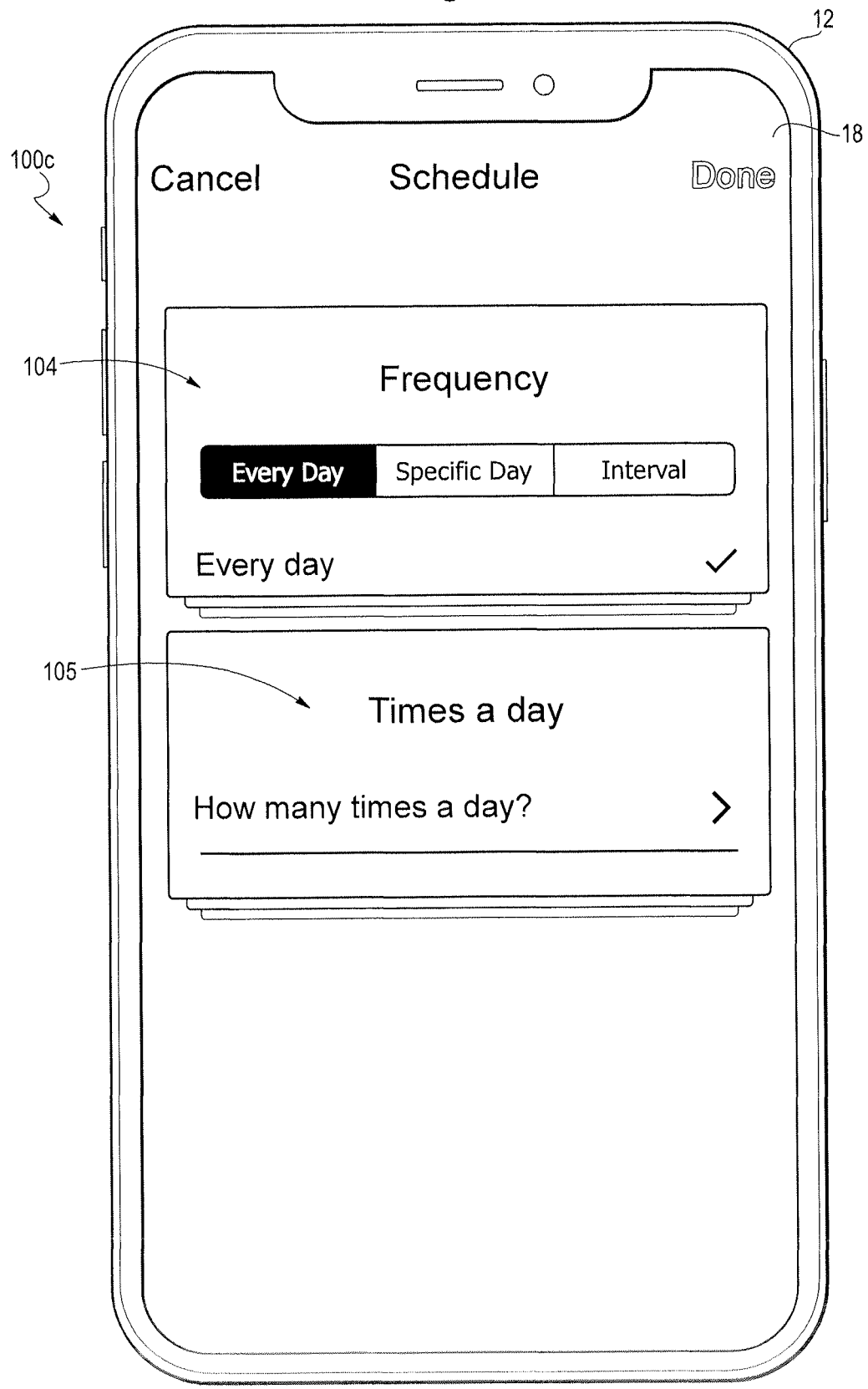
FIG. 7 is a front elevation view of a user input screen for medication schedule in accordance with an embodiment of the present disclosure.
Figure 8:
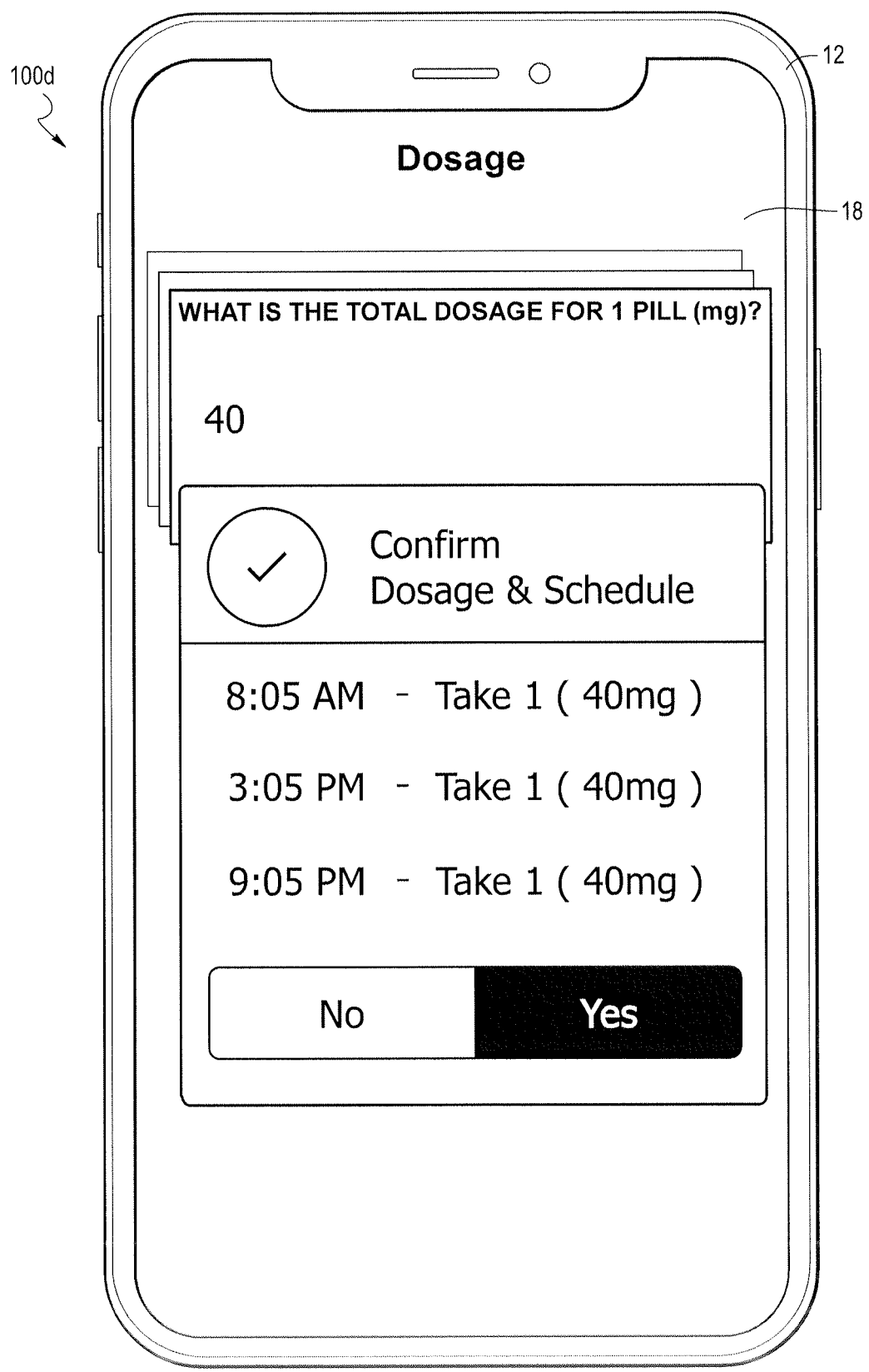
FIG. 8 is a front elevation view of a user input screen for dosage and schedule in accordance with an embodiment of the present disclosure.

At step 102 (FIG. 4 and FIG. 6 display screen 100b), the user enters the medication type as shown in FIG. 6 screen 100b. Typical medication types include pill and liquid (shown on screen 100b as "pill" or "cc" or "ml"). Other medication types include, spray, cream, drops, pieces, teaspoon, tablespoon, meq, puffs, spray, patch, etc. In an embodiment, at step 102, the dose-app determines the appropriate algorithm (motion detection algorithm) for the medication type by prompting the user to select an image of the corresponding medicine container that houses the type of medication chosen. For example, if a user selects "pills" at step 102, the user is then prompted with images of different types of medication containers that are known to hold pills. The user then selects the appropriate medication container matching the user's actual medication container. The dose-app 18 stores the user-inputted medication name and medication type in memory.

At step 103 (FIGS. 4 and 7), the Schedule option enables the user to input (i) the frequency of the dose (i.e., every day, specific days, interval (i.e., every day, every second day, every third day, etc.)) (ii) the number of dosages per day (one dose per day, two doses per day, three doses per day, etc.) (iii) what time per day (morning, afternoon, before bedtime, with/without food, etc.), (iv) how many units per dose (pills at dose time), and any combination of (i)-(iv) as applicable for the specified medication. The user enters the medication schedule as shown on screen 100c in FIG. 7.

At step 104, the user enters the frequency for medication dosage (i.e., every day and number of times per day, specific days, interval (every other day)). At step 105, the user enters the time of day for the medication dosage (i.e., morning, evening, just before bedtime) as applicable. At step 106, the user enters the quantity per dosage (one pill, two pills). The dose-app 18 stores all the foregoing user-inputted medication information in memory.

At step 107 (FIGS. 4 and FIG. 7 display screen 100c) the Dosage option provides one or more display screens which prompt the user to input the dosage for the medication. At step 107, the user is prompted to enter the dosage amount to match the selected in option at step 102. Nonlimiting examples of dosage options include, 100 mg, 200 mg, 20 ml, 50 ml. At step 108 (FIG. 8 display screen 100d), the user is prompted with a display screen to confirm the dosage and schedule entered for the medication.

The dose-app stores the user-inputted medication information in memory.

In an embodiment, the dose-app includes a database of medications which the user can select from a drop-menu. Selection of the medication populates the medication type (pill, liquid, spray).

In an embodiment, the dose-app downloads and imports the patient's medication data for steps 101 through 108 by communicating with a database stored on an external server, such an external server with a database storing electronic health records, for example.

At step 109, the user has the option of entering additional information such as "take on empty stomach" or "take with food") or other helpful tips.

5. Refill

With user selection of a "Refill" option, the dose-app provides one or more display screens which prompt the user to input the number of refills available for the medication. Nonlimiting examples for mechanisms for the user to enter the number of refills include (i) hand type dosage into screen, and (ii) select dosage from a dropdown menu. The dose-app stores the user-inputted dosage in memory.

In an embodiment, when it is time for a refill, the dose-app sends a notification to the user that a re-fill of the medication is due. The dose-app automatically notifies the patient's pharmacy that a re-fill is required by communicating with an external server via the Internet, for example.

6. Synchronization

With completion of the "Enter Medication" inputs into the dose-app 18 on the mobile device 12, the dose-app 18 is then synchronized with the motion detection component 16a. The term "synchronization," (or "sync") as used herein, is the pairing of a specified user-inputted medication entered into the dose-app to a specified dedicated motion detection component. In other words, the "sync" function wirelessly matches a user-inputted medication in the dose-app 18 to a dedicated motion detection component 16a (and dedicated medication container 14a).

In an embodiment, the dose-app 18 includes an iBeacon protocol. An "iBeacon protocol," as used herein, is a Bluetooth-based communication protocol that enables hardware transmittals "Beacons" ("Beacons" hereafter interchangeably referred to as the MDCs) to broadcast their identity to a nearby mobile device. The iBeacon protocol enables mobile devices such as smartphones and tablets to perform actions within the local area of the Beacon. The iBeacon protocol interfaces with, and utilizes, "Location Services" and the Bluetooth functionality on the mobile device, the iBeacon protocol enabling the dose-app to detect, and wirelessly communicate with, one or more nearby MDCs ("Beacons").

The iBeacon protocol includes three identifiers that are constantly broadcasted from each Beacon (MDC). When the user enters or exits the local area, the dose-app 18 is notified. The user is prompted to open the dose-app via a notification sent to the mobile device. When the user selects the notification to open the dose-app from the lock screen, or the user manually opens the dose-app by opening the lock screen and then selecting the dose-app icon, the dose-app changes from operating in the background to operating in the foreground. When the dose-app is operating in the background, the dose-app can only read three advertising identifiers: proximity UUID, a major value and minor value.

The first identifier is a proximity universally unique identifier or "UUID" which is a 128-bit value that uniquely identifies each Beacon as a certain type of Beacon, or a Beacon from a certain organization. The second identifier is a major value, which is a 16-bit unsigned integer that can be used to group related Beacons that have the same proximity UUID. The third identifier is a minor value, which is a 16-bit unsigned integer that differentiates Beacons with the same proximity and major value.

In an embodiment, each Beacon (MDC) has its own UUID, the major value is set to zero and the minor value is set to zero.

The iBeacon protocol enables wireless communication between a Beacon (i.e., the MDC 16a) and a nearby mobile device. The MDC 16a transmits its UUID to the local area. If more than one MDC are present, each MDC transmits its own UUID to the local area, via Bluetooth wireless communication. The UUID is detected by the dose-app 18 residing on the mobile device when the mobile device is in the local area. With detection of the UUID, the dose-app 18 determines the MDC's physical location. The iBeacon protocol is compatible with iOS software.

Figure 9:
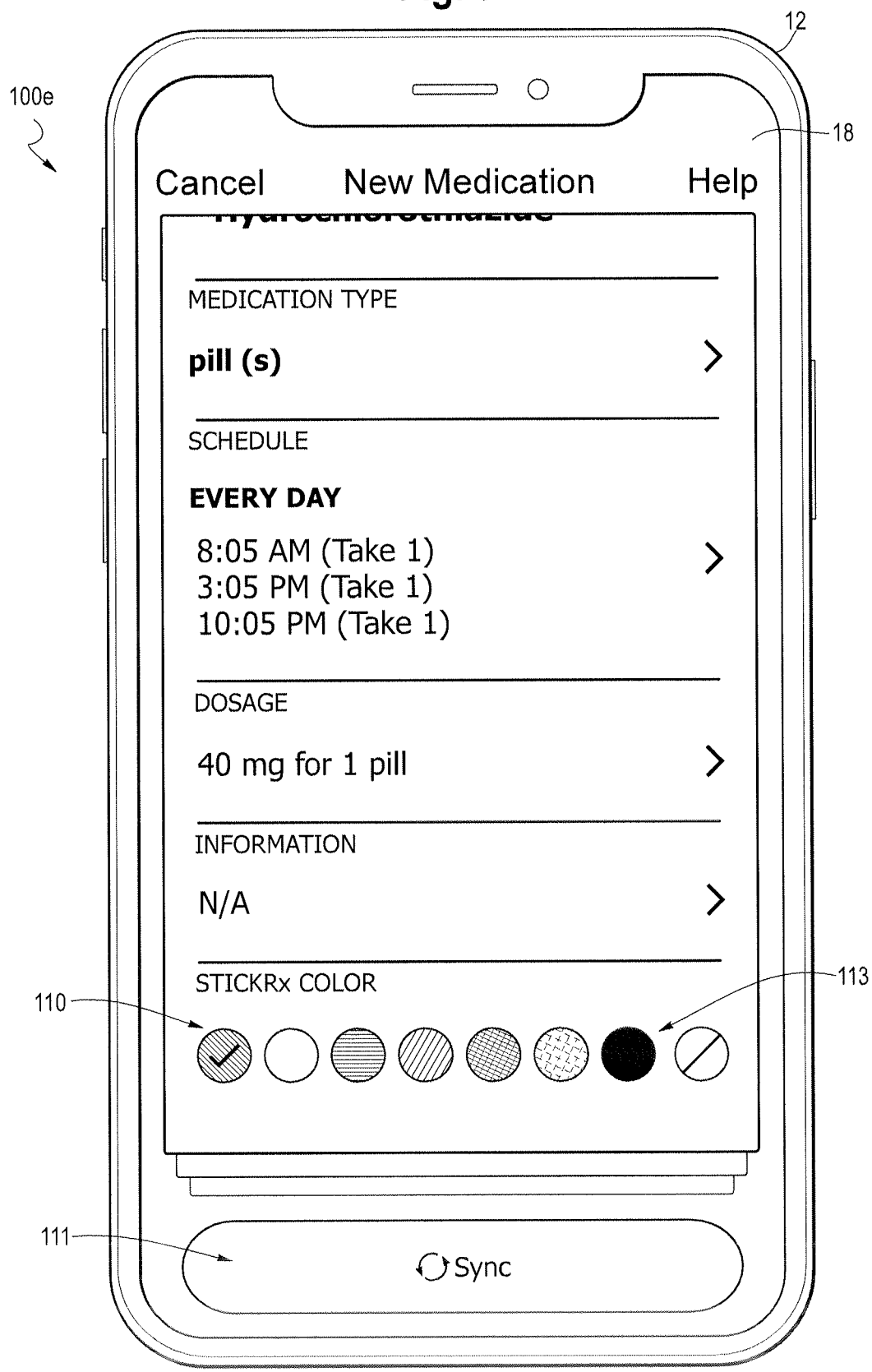
FIG. 9 is a front elevation view of a user input screen for selecting motion detection component color and synchronizing the dose-app with the motion detection component, in accordance with an embodiment of the present disclosure.

At step 110 (FIG. 4 and FIG. 9 display screen 100e), the user selects the color of the MDC housing as explained below. Once the color is assigned, this color can no longer be selected. With user selection of the color (i.e., "Choose STICKRx Color" as seen in FIG. 9), the user attaches the medication detection component on the medication container 14a.

Here, the dose-app provides a pop up with instructions to the user for attachment of the MDC 16a onto the medication container 14a. For example, when the medication container is a medication bottle with a screw on cap, the dose-app provides instructions to the user to attach the Beacon to the top of the screw cap. The instructions may be text, a drawing, or a combination thereof. By way of further example, when the medication is albuterol and the medication container is a boot-type inhaler, the dose-app instructs the user to attach the Beacon (MDC) to the boot-type inhaler. By way of yet further example, if the medication is a topical cream and the medication container is a squeeze tube, the dose-app instructs the user to attach the Beacon on the squeeze tube.

At step 111 (FIGS. 4 and 9), the user selects the "sync" icon on the dose-app 18. With selection of the "sync" icon, the dose-app 18 then searches for nearby motion detection component(s) (step 112 of FIG. 4) using the iBeacon protocol.

Each MDC in the local area wirelessly broadcasts data by way of Bluetooth low energy. Data broadcast by the motion detection components(s) includes a unique universal identifier (UUID), and Beacon name.

At step 112, the dose-app 18 searches for the UUID and the name of one or more MDCs. Each MDC has a unique identifier (i.e., a sticker with an identification name and/or number) and a unique housing color. Although each MDC has a unique UUID, MDCs of the same unique identifier are assigned the same name. For example, all blue MDCs are given the name "S001." When the user selects the blue MDC, the dose-app starts searching and requesting the MDC name for all MDCs in the local area. Once the dose-app finds the MDC with the correct name based on what the user selected in step 110, the dose-app syncs with that MDC's (Beacon's) UUID. This synchronization protocol occurs unpronounced to the user. If no MDC is found, the dose-app continues to search for a MDC (step 114 and return back to step 112).

At step 115, the dose-app 18 color codes the medication information with the color of the synchronized MDC housing. For example, FIG. 9 shows user selection of the leftmost circle, which is a blue-colored circle (the presence of a check mark in blue-shaded circle for "STICKRx Color") for the MDC 16a. The dose-app 18 matches the same color (blue) of the synced MDC 16a housing to screens of the mated medication. In other words, the MDC 16a housing is blue which is synchronized with all of the user-inputted medication information for "Hydrochlorothiazide." The dose-app 18 applies a blue background color for the display screens associated with the Hydrochlorothiazide medication information.

At step 115, the UUID of the MDC is paired with the user-inputted medication information (steps 101-109) in the dose-app 18. By way of example, the UUID of MDC 16a (with blue housing) is paired with all the medication information for Hydrochlorothiazide. In this way, the user-inputted medication is matched ("synced") to a specified and dedicated individual MDC in the dose-app. The dose-app 18 displays "sync successful" (step 115) on the mobile device display.

Figure 10:
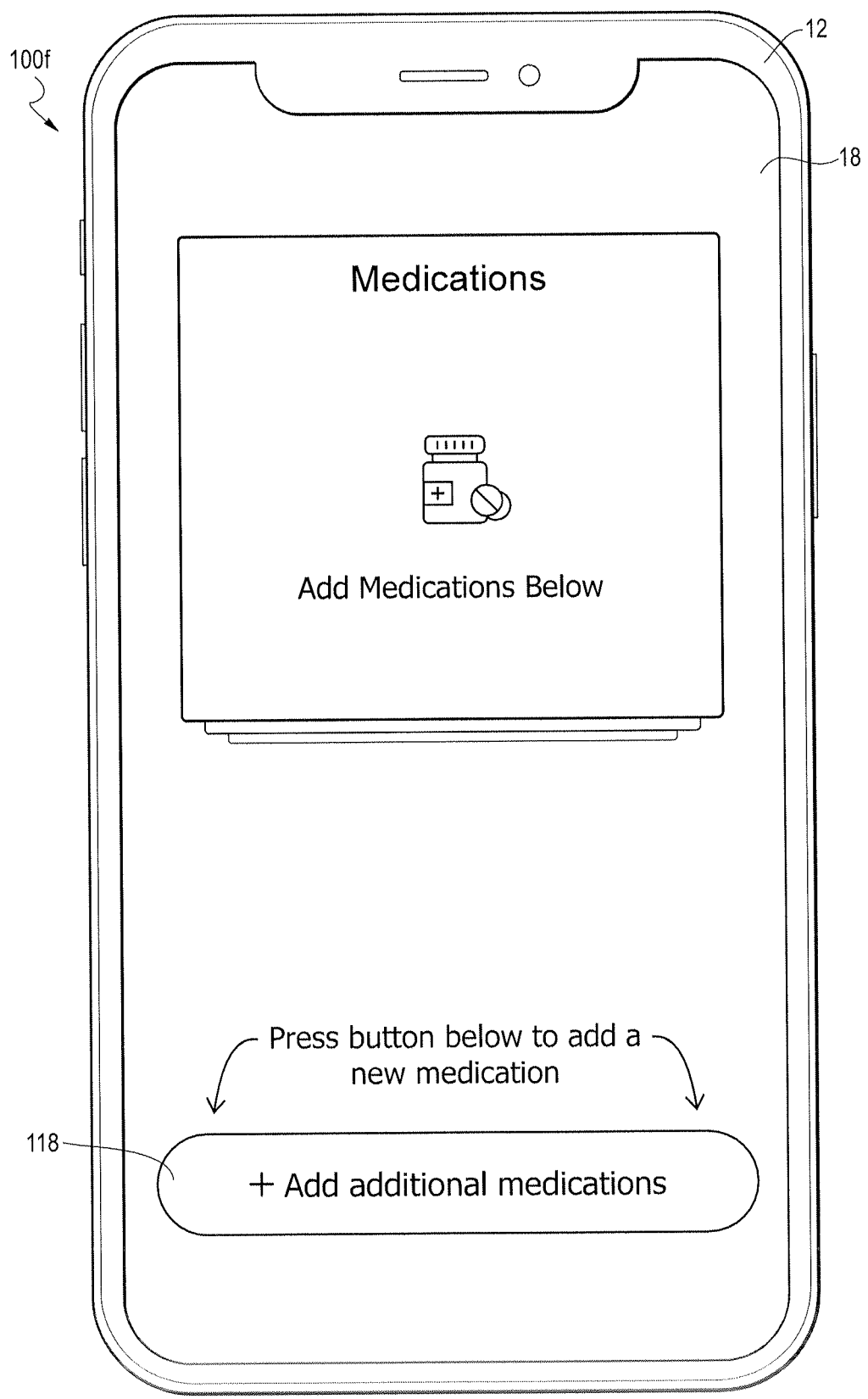
FIG. 10 is a front elevation view of a user input screen for entering additional medications into the dose-app in accordance with an embodiment of the present disclosure.

FIG. 10 shows display screen 100f whereby the user can select an "Add additional medications" icon 118. Selection of icon 118 takes the user back to steps 101-115 so that the user can enter additional medication information and synchronize with additional MDCs by repeating steps 101-115.

Figure 11:
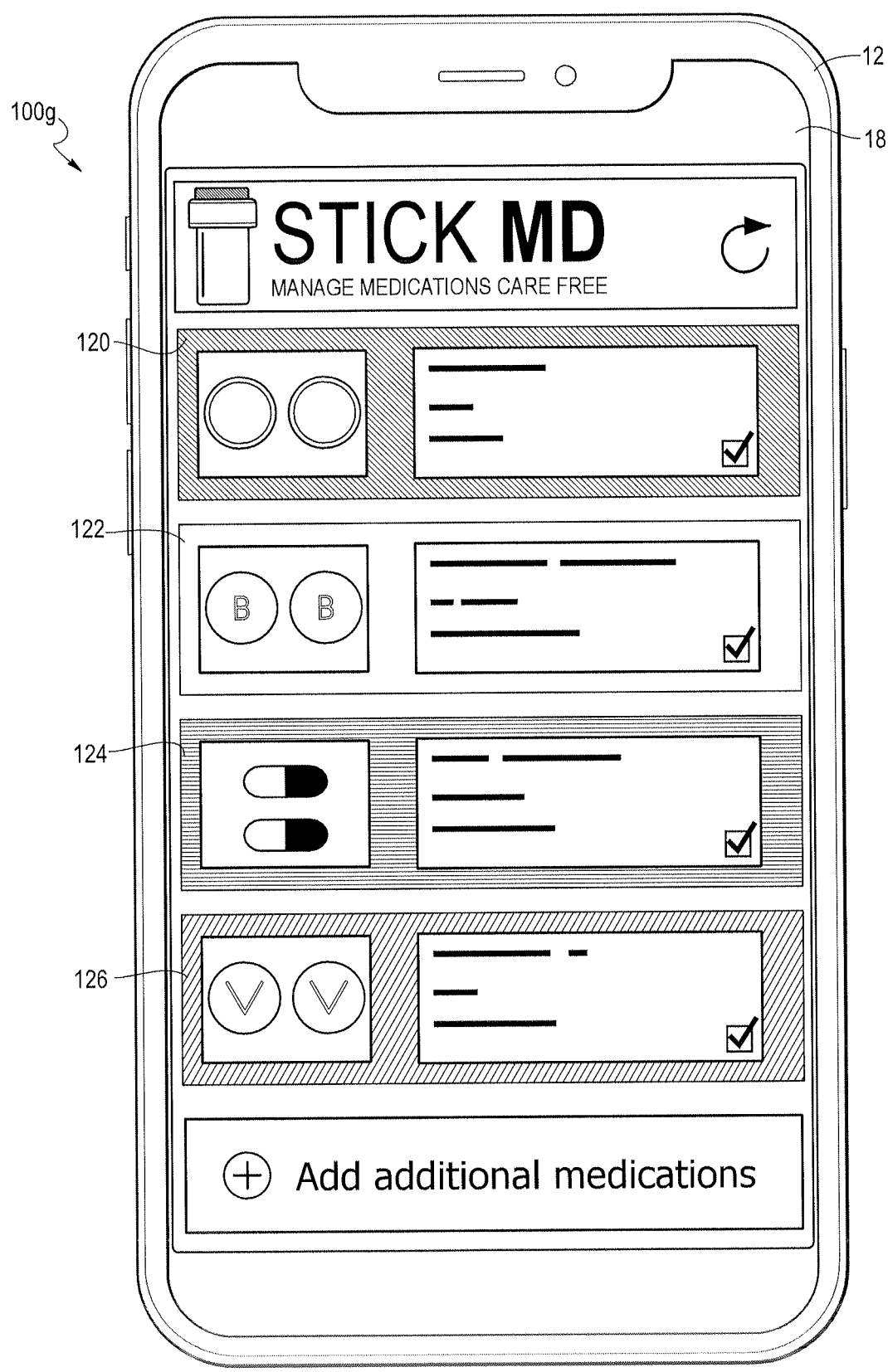
FIG. 11 is a front elevation view of a user input screen showing four medications entered into the dose-app in accordance with an embodiment of the present disclosure.

FIG. 11 shows a nonlimiting example whereby display screen 100g shows dose-app 18 synchronized for four different medications. On the mobile device display screen 100g the medication Hydrochlorothiazide (with blue background) 120 is synchronized with a first MDC having a blue housing (MDC 16a). A second medication ("B pills") with red background 122 is synchronized with a second MDC having a red housing. A third medication (capsules) with a green background 124 is synchronized with a third MDC having a green housing. A fourth medication ("V-pills") with yellow background 126 is synchronized with a fourth MDC having a yellow housing.

7. Multiple Medications

An advantage of the present system is the ability to alert, track, monitor, and verify dosage for one, two, three or more medications for a user. The user repeats steps 101-115 for each medication. In this way, the user pairs one, two, three or more specific motion detection components with respective one, two, three or more respective medication/medication container(s). The present system is advantageously applied when the user has two or more medications to take.

When the user has two or more medications to take, the user selects from a plurality of MDCs, the housing of each MDC having a distinct and different color. In an embodiment, the user orders a kit with two or more motion detection components. The housing for each motion detection component in the kit has a distinct color such as black, white, green, blue, red, orange, yellow, purple, pink, etc.

8. Operation of System

Figure 12:
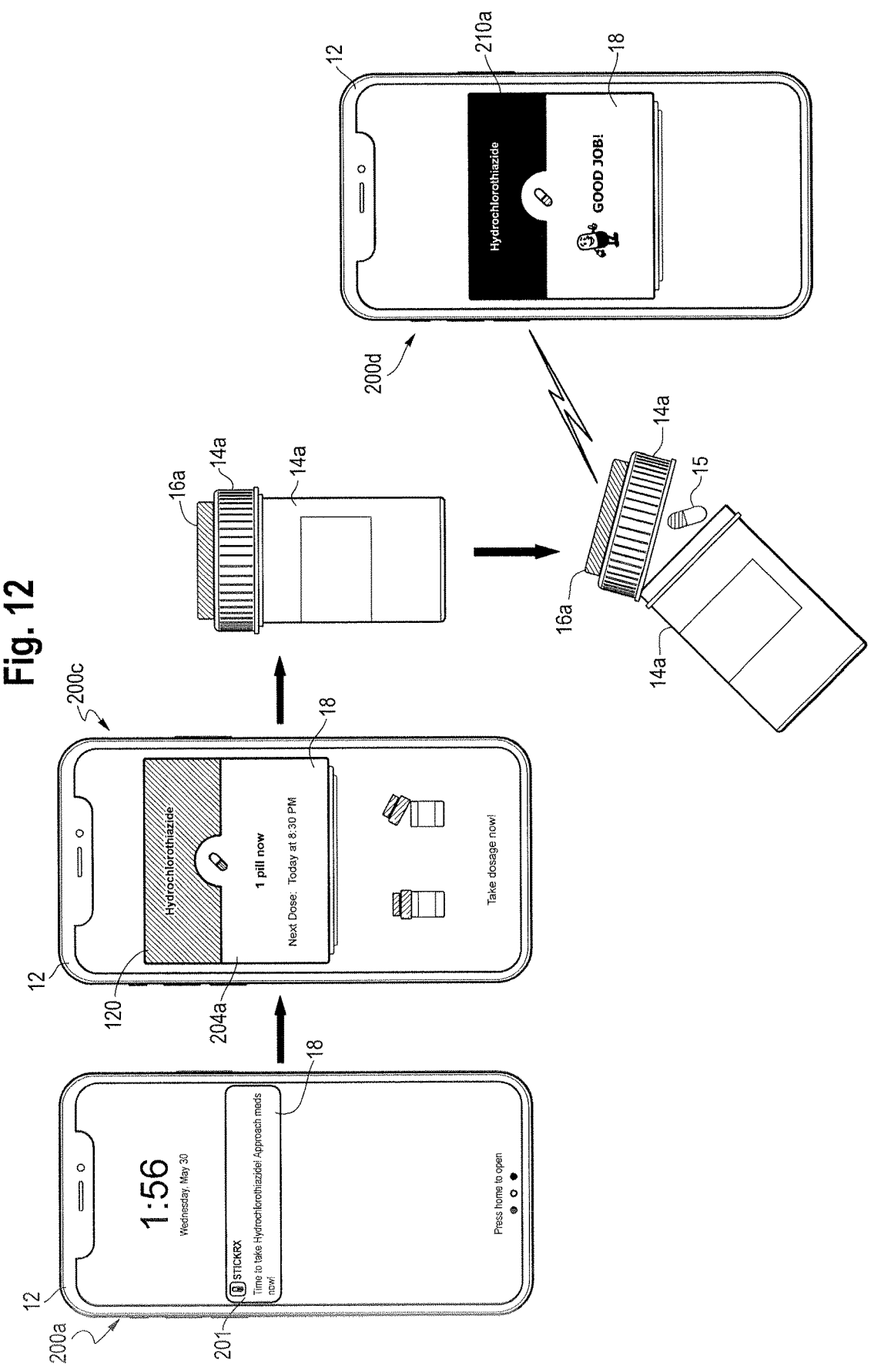
FIG. 12 is a perspective view of the system notifying a user to take a medication and the system monitoring the dose event with the motion detection component, in accordance with an embodiment of the present disclosure.

With the medication information input into the dose-app 18, the dose-app 18 synchronized with a dedicated MDC 16a (and dedicated medication container 14a), and the MDC 16a attached to its respective medication container 14a, the present system is ready for operation. FIG. 12 shows the dose-app 18 alerts the user with a notification 201 when it is time for the user to take a given medication. The notification 201 appears on the home screen of the mobile device 12. The notification can be a text message alone or in combination with an image of the medication and/or MDC housing color, an audio notification, a tactile notification (i.e., vibration), and any combination thereof.

The notification 201 prompts the user to proceed toward the medication container 14a with the designated MDC 16a attached thereto. In this nonlimiting example, a notification on the mobile device 12 notifies the user that it is time to take Hydrochlorothiazide and indicates the medication name and the MDC 16a color (blue).

Upon receipt of the notification 201, the user (carrying the mobile device) proceeds toward the medication container with the blue MDC 16a. Once the user gets within the local area of the medication container 14a/MDC 16a, the motion detection device 26 transmits motion data to the dose-app 18 by way of the WCC 28. The dose-app 18 receives the data from the MDD. The dose-app 18 includes one or more algorithms for interpreting the motion data.

Applicant discovered that the user's handling of the medication container in order to dispense the medication therefrom subjects the medication container to a unique array of movements. By attaching a MDC on a given medication container, movement in the x-, y- and z-axes imparted upon the medication container by the user during dispensing of the medication can be measured and recorded. For example, each particular medication container—screw-cap container, blister pack, and inhaler—exhibits a distinct array of movements in the x-, y- and z-axes when a user dispenses medication therefrom. For example, dispensement from the screw-cap container requires an unscrewing motion. Dispensement from the blister pack requires a pushing motion to break the backing material and release a pill from a blister cavity. Dispensement of an aerosol from an inhaler requires a pumping motion. An MDC attached to each particular medication container can detect and record these movements of the container in three dimensions. These movements can be detected by the MDD and recorded and transmitted to the dose-app 18 for interpretation.

9. Algorithm

Provided within the dose-app 18 is one or more algorithms. Each algorithm is embodied in code instruction and is generated based on predetermined 3-axis motion profile for a specified medication container dispensement.

In other words, each algorithm can be quantified, or otherwise tailored, into a unique motion profile for each type of medication container.

As the 3-axis motion data is transmitted from the MDC to the dose-app, the algorithm is interpreting the motion data in real-time. If the algorithm determines the motion data fulfills the motion profile for proper dispensement of the medication, it can be measured and quantified. With a MDC attached to the screw-cap of a screw-cap container for example, Applicant discovered the motion profile for unscrewing the cap in order to dispense a pill can be detected, recorded, and the unscrewing motion can be distinguished from other types of container movement. In other words, the motion profile for dosage of the medication can be separated, or otherwise distinguished from other types of container motion, such as a fallen container, tipped container, carried container and other types of movement "noise."

A "motion profile" as used herein, is the waveform created by accelerometer readings over a defined period of time in the x-axis, y-axis, and z-axis of the MDC during the movement of a given medication container.

As the user handles the medication container to dispense the medication, the MDD transmits motion data to the dose-app. The algorithm in the dose-app interprets, or otherwise analyzes the motion profile to determine whether the motion data from the MDD matches the motion profile for a valid medication dose.

The algorithm is embedded into the dose-app; the algorithm is constructed from the following blocks (A-E).

Block A. A binary statistical hypothesis test is created with a null hypothesis (HO) and an alternate hypothesis (Ha). The null hypothesis (HO) is associated with "no dose" such as dropping, tipping, and/or spilling of the medication container. The alternate hypothesis (Ha) is associated "valid dose" (i.e., unscrewing the cap, for example). It is understood that the HO and the Ha can be created for other containers with different ways to dispense a dose.

Block B. Models (waveforms, motion profiles) are created from pre-recorded motion data. The null hypothesis (HO) is created from waveform data representing "no dose" i.e. tipping over. The alternate hypothesis model is created from waveform data of "valid dose" i.e. the cap being unscrewed from the container.

Block C. From the recorded data, maximum likelihood estimates are computed for the unknown parameters in each of the models—the HO model and the Ha model.

Block D. The estimated values in (Block C) are used to compute a log-likelihood ratio, hereafter referred to as the likelihood ratio LR. The "likelihood ratio" or "LR" is the natural log of the ratio of the probability of the observed data given HO to the probability of the observed data given Ha.

Block E. The null hypothesis HO is rejected if the probability of the log likelihood ratio is greater than the computed log likelihood ratio is less than "p". When the null hypothesis is rejected, the dose-app registers the motion profile as a valid medication dose or a "valid dose." If the null hypothesis is not rejected, the dose-app registers the motion profile as an invalid medication dose or "no dose." The term p is an acceptable trade between the probability of false alarm and the probability of detection.

In the event the user handles the wrong medication container, the dose-app 18 transmits an alarm to prevent the user from taking the wrong medication at the wrong time. The alarm emitted from the mobile device can be an audio alarm, a visual alarm (blinking light), and a tactile alarm (vibration), and combination thereof.

10. Compliance

The dose-app 18 enables the user to track and monitor his or her adherence to the medication protocol on a daily, weekly, or monthly basis. In an embodiment, the dose-app 18 communicates with one or more other computing devices. Communication may be by way of wired communication or wireless communication (Wi-Fi, Internet, Bluetooth, etc.)

In an embodiment, the dose-app 18 is configured to communicate with a central server. The dose-app 18 sends dose event ("valid dose" or "no dose") data to the central server. The dose event data ("valid dose" or "no dose") can be monitored by a third party as desired by the user or the patient. A "third party," as used herein, is a person or entity other than the person ingesting the medication(s), hereafter referred to as the patient. Nonlimiting examples of a third party include spouse of patient, child of patient, other family member(s) of patient, friend of patient, healthcare provider, insurer of patient, agent of the patient, and any combination thereof.

Medication dosage can occur in (i) iBeacon Protocol or (ii) Core Bluetooth Protocol. In either mode, motion data is transmitted from the MDD to the dose-app in order to validate and/or verify whether a valid dose event occurred.

Figure 13:
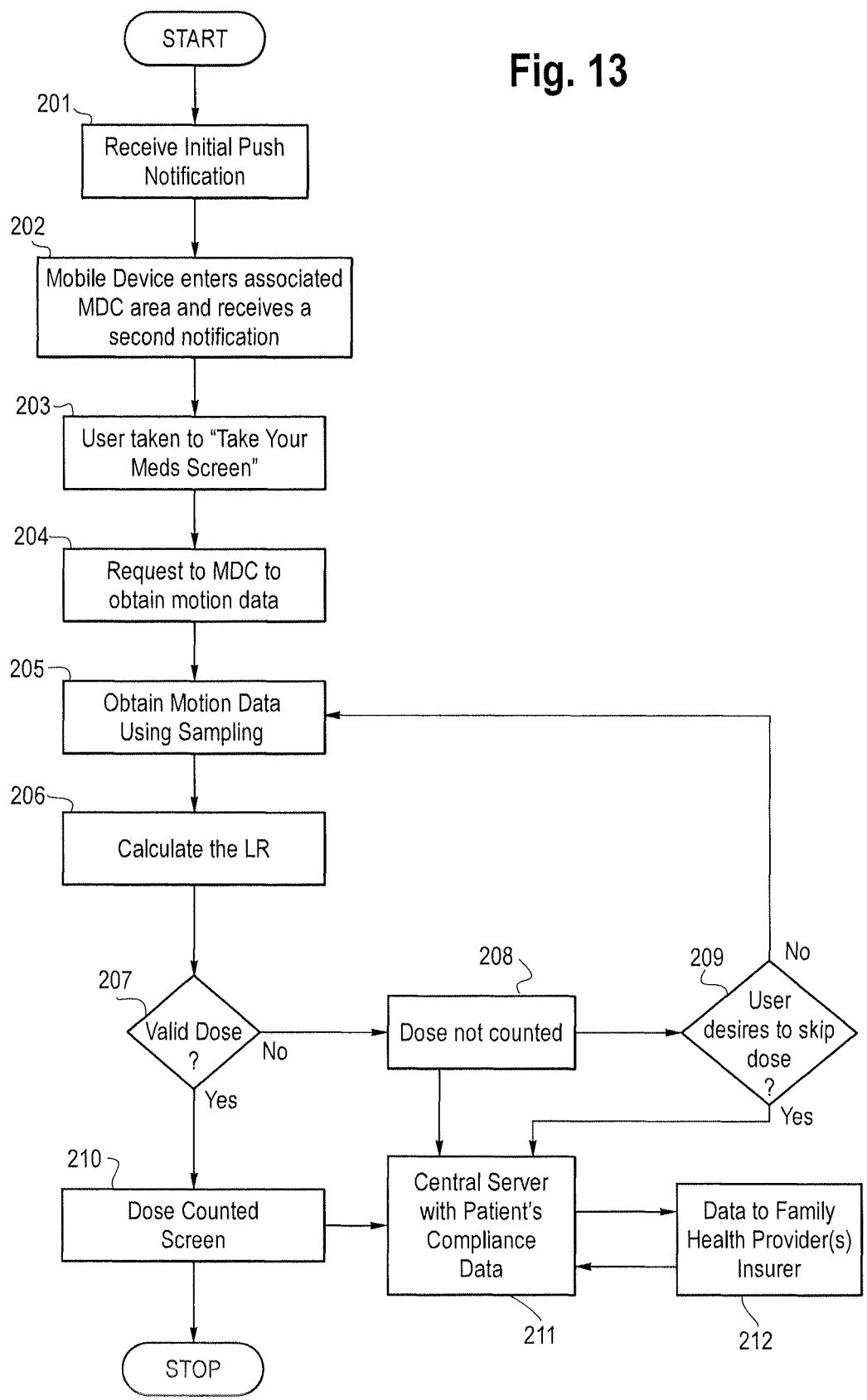
FIG. 13 is a flowchart illustrating a process for managing medication with the dose-app and the motion detection component in accordance with an embodiment of the present disclosure.
Figure 16:
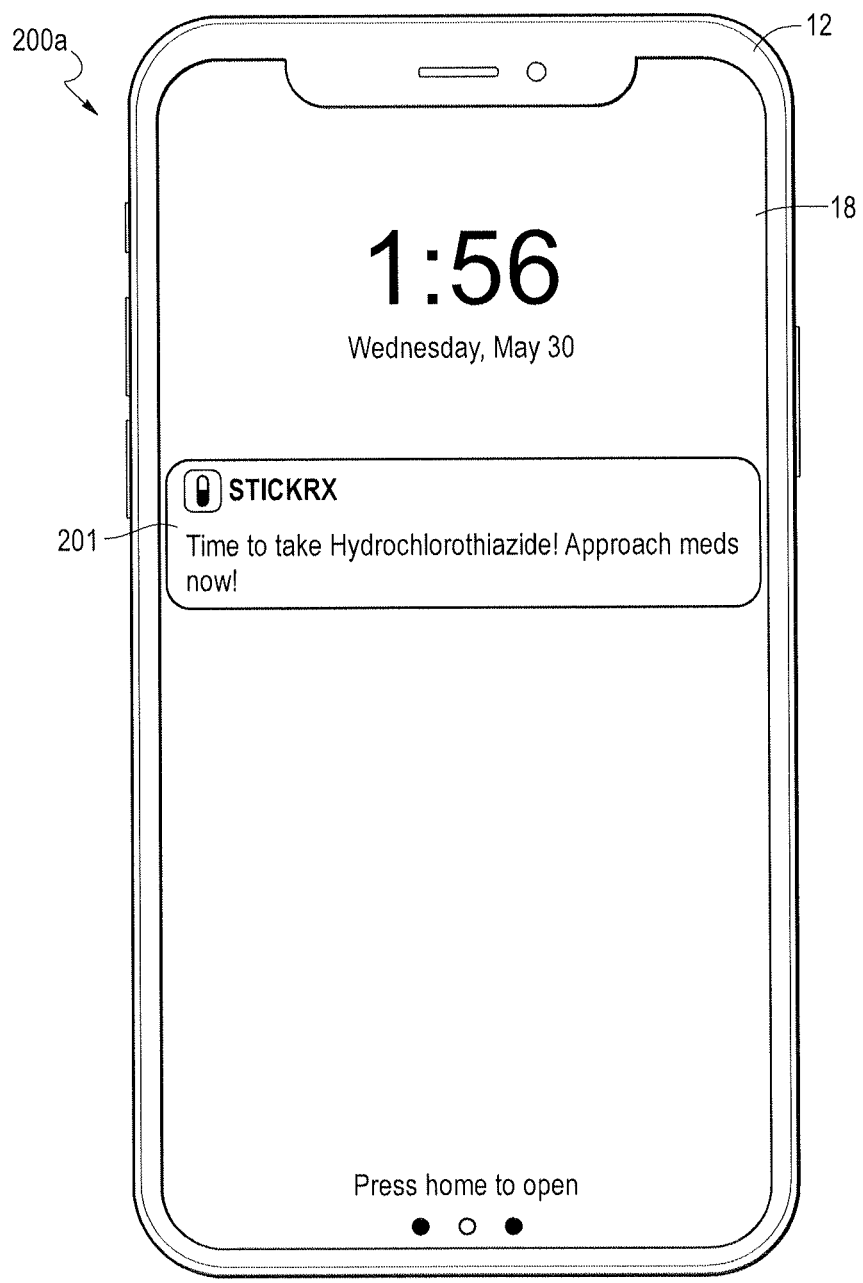
FIG. 16 is a front elevation view of a display screen showing a notification in accordance with an embodiment of the present disclosure.

FIG. 13 shows the operations performed by the system 10 when operating in the iBeacon Protocol. When the mobile device 12 is interacting with the motion detection component as in iBeacon Protocol, the system performs the following functions as shown in FIG. 13. At step 201 of FIG. 13, the dose-app 18 delivers a notification 201 (FIG. 12 and FIG. 16 display screen 200a) to the user that it is time take a medication based on the time inputted into the dose-app. FIGS. 12 and 16 show display screen 200a. A nonlimiting example of notification 201 is "Time to take Hydrochlorothiazide. Approach Meds now" as shown in FIGS. 12 and 16.

When the user reads notification 201, the user moves to the local area as shown is step 202 of FIG. 13. When the user is in the local area (i.e., within the wireless transmission range of the MDC 16a), the dose-app 18 displays a second notification 202 identifying the medication to be ingested and container from which dosage is to be performed.

Figure 17:
FIG. 17 is a front elevation view of a display screen showing a notification in accordance with an embodiment of the present disclosure.

FIG. 17 shows display screen 200b with a nonlimiting example for second notification 202: "Blue STICKRx: 5 mg for 1 pill now! Press and Hold to Open!"

At step 203, the user opens the locked screen by (i) clicking directly on notification 202 on the lock screen or (ii) by way of the pop down notification if the user is on the mobile device during the time of the notification 202. The user can also access the "Take Your Meds Screen" by opening the dose-app 18 and clicking on the medication that is highlighted by a notification logo next to the correct medication.

Figure 18:
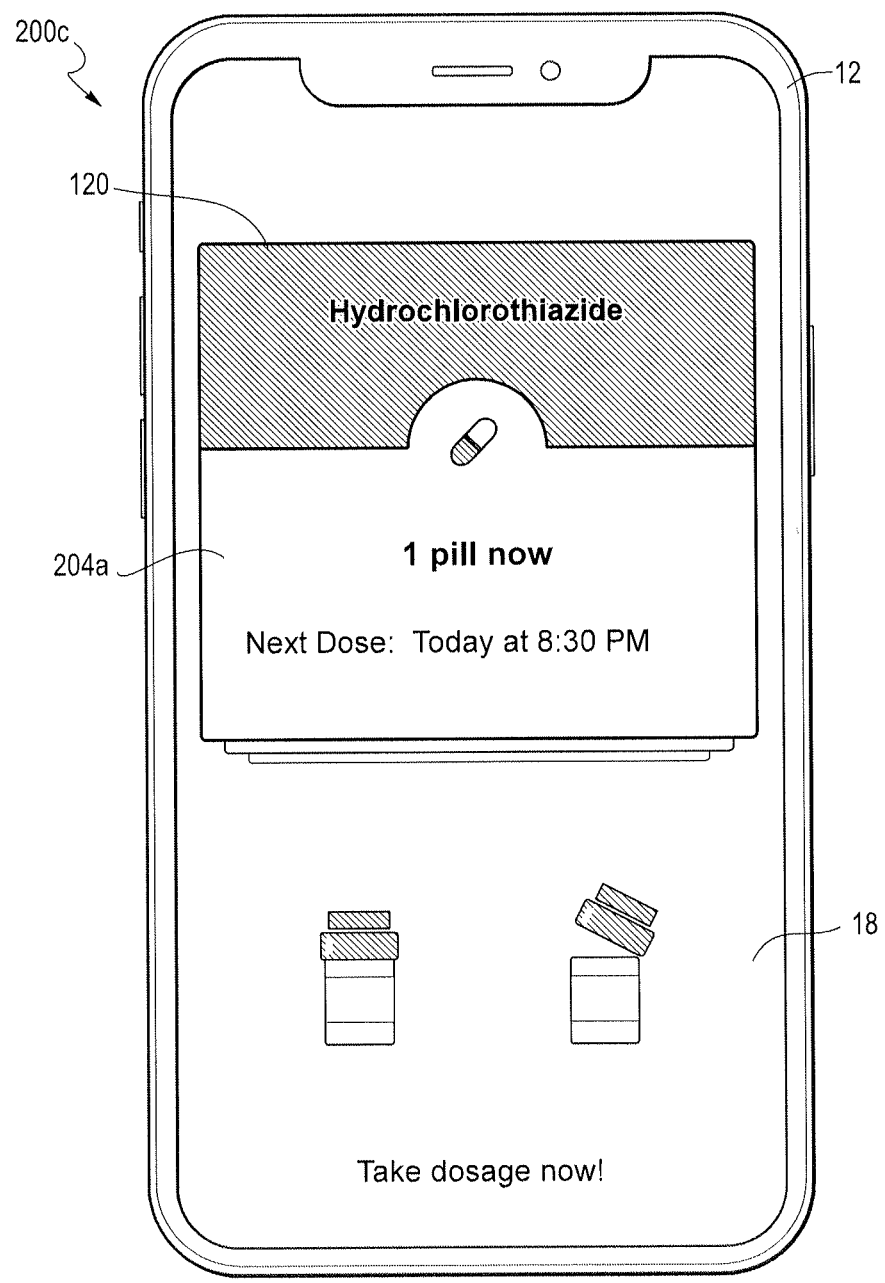
FIG. 18 is a front elevation view of a display screen showing a notification in accordance with an embodiment of the present disclosure.

In step 204, display of "Take your Meds Screen" on the mobile device 12 triggers the dose-app 18 to send a request to the MDC 16a for motion data as shown in FIG. 12. A nonlimiting example of a "Take your Meds Screen" is shown in FIGS. 12 and 18 where display screen 200c shows notification 204a with the name and dosage of the medication—"Hydrochlorothiazide, 1 pill now"—displayed in the background color that is the color of the MDC housing—in this example notification 204a's blue background 120 matches the MDC 16a housing color which is blue. The dose-app 18 receives motion data from the MDD and the algorithm in the dose-app calculates the likelihood ratio (or "LR") as shown in steps 205, 206 of FIG. 13.

The algorithm embedded in the dose-app calculates the likelihood ratio in step 206. Based on the motion data received from the MDC, the algorithm determines whether a "valid dose" occurs or whether "no dose" occurs, step 207.

When "no dose" is determined (step 208), the dose-app 18 displays a notification on the screen of the mobile device 12 asking the user whether the user would like to skip the dose (step 209). If the user selects "yes, skip the dose," the event is registered as "no dose." The user has a set amount of time in which not responding to the notifications will also result in a "no dose." If the user has activated the share plus notification feature, notification of the dose event can be sent to third parties, the user's family, health provider(s), and insurer and transmitted to a server as shown in step 211.

If the user selects, "no, do not skip dose," the dose-app 18 directs the user back (directs the user back to step 205) where the mobile device 12 triggers the dose-app 18 to send a request to the MDC for motion data.

Figure 19:
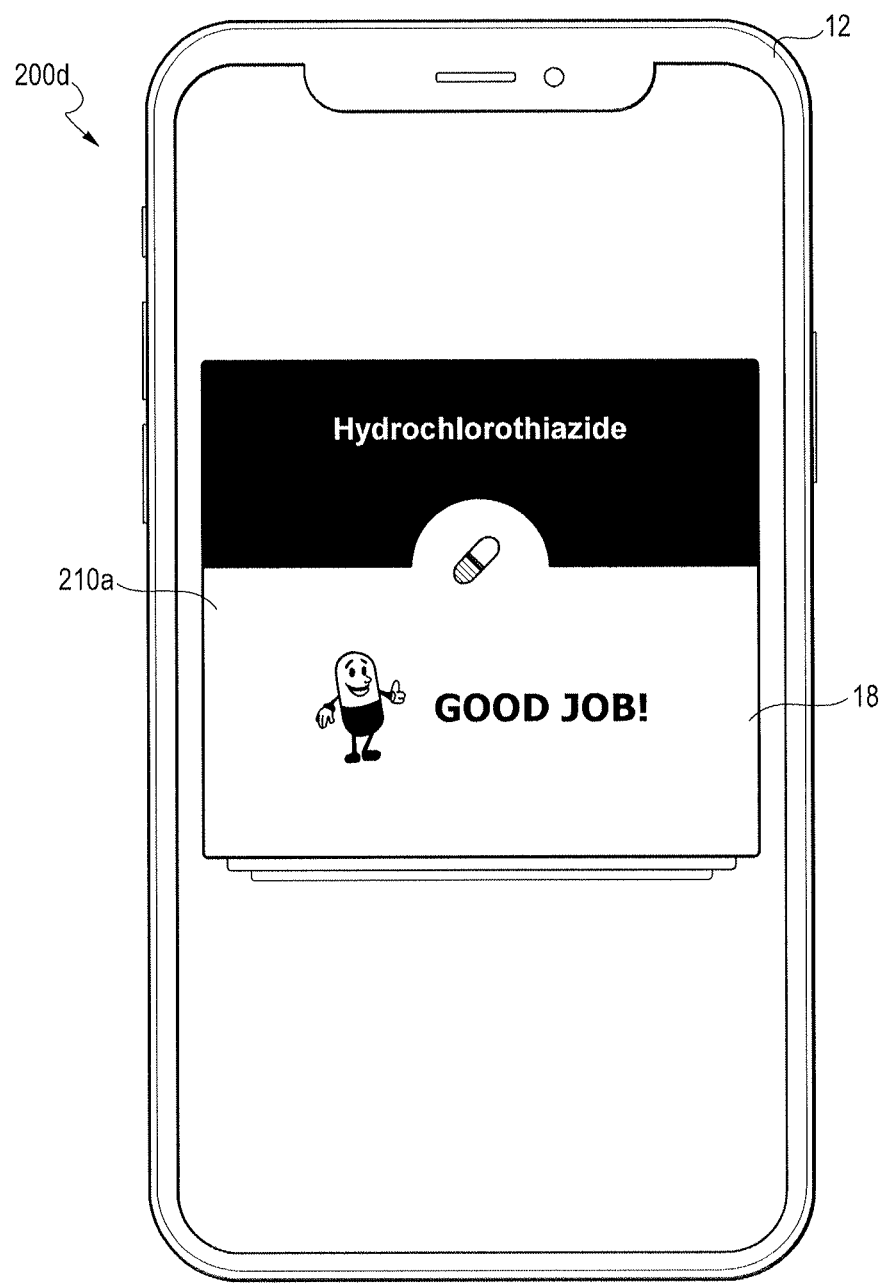
FIG. 19 is a front elevation view of a display screen showing a notification in accordance with an embodiment of the present disclosure.

When "valid dose" is determined by the algorithm, the dose-app 18 displays a confirmatory screen on the mobile device (step 210). The screen turns green and informs the user that the medication has been taken. A nonlimiting example of a confirmatory screen is shown in display screen 200d in FIGS. 12 and 19 where confirmation 210a indicates the name of the medication—in this example, "Hydrochlorothiazide" in a green background (the color green indicating success)—and the message "Good Job!" The "valid dose" is registered in the dose-app 18. If the user has agreed to share dose event information to her third parties, the dose-app 18 sends the dose event data to the central server (step 211). The third parties can access the compliance data at any time and see how the user is doing (step 212).

11. Core Bluetooth Protocol Pathway

In an embodiment, the mobile device may interact with the MDC by way of core Bluetooth protocol pathway. Core Bluetooth protocol pathway enables the dose-app on the mobile device to communicate with Bluetooth low energy devices. Bluetooth low energy communication involves two components: (i) a central device (i.e., the mobile device), and (ii) a peripheral device (i.e., the MDC). Core Bluetooth protocol pathway is based on a client-server architecture, whereby the peripheral device typically has data that is needed by other devices. The central device typically uses the information served up by peripheral device(s) to accomplish some particular task. The peripheral device(s) broadcast some of the data they have in the form of advertising packets. An advertising packet is a relatively small bundle of data that may contain useful information about what a peripheral device has to offer, such as the peripheral device's name and primary functionality. A central device, on the other hand, can scan and listen for any peripheral device that is advertising information. The central device can pair to the peripheral device by searching for its UUID. After pairing, the central device can request connection to the peripheral device and receive data from the peripheral device.

Figure 14:
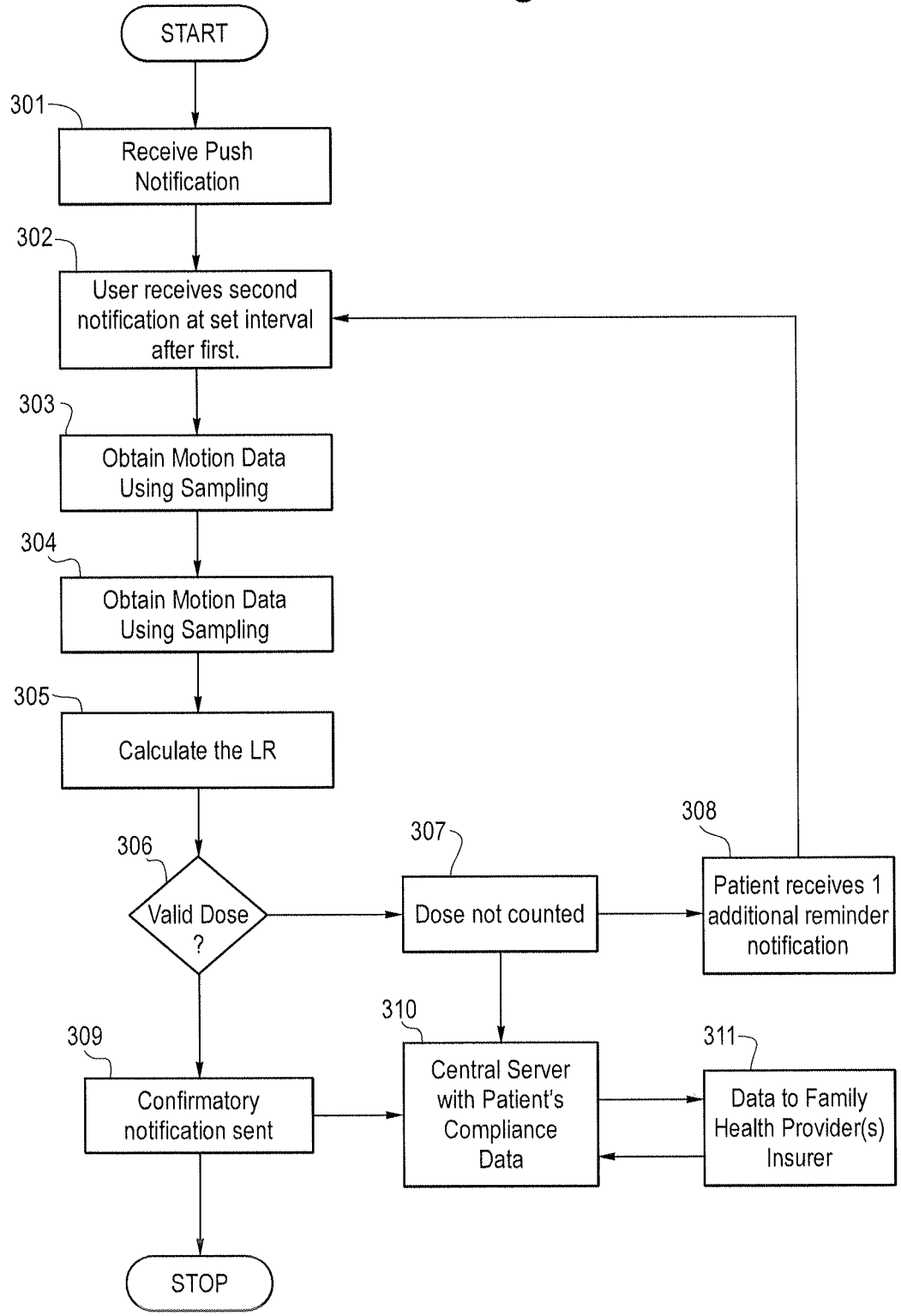
FIG. 14 is a flowchart illustrating a process for managing medication with the dose-app and the motion detection component in accordance with an embodiment of the present disclosure.

When the mobile device is interacting with the MDC in core Bluetooth protocol, the system 10 performs the following functions as shown in FIG. 14. At step 301 of FIG. 14, the dose-app delivers a notification ("notification 1") to the user that it is time take a medication based on the time inputted into the dose-app. Notification 1 can be the same as, or different from, notification 201 as shown in display screen 200a of FIG. 16. A nonlimiting example of notification 1 is "Time to take [insert medication name.] Approach Medication now."

After a set interval of time, (i.e., 15-30 seconds), the dose-app 18 displays notification 2. Notification 2 identifies the medication to be ingested and the medication container from which the dosage is to be performed. Notification 2 can be the same as or different from notification 202 as shown in display screen 200*b* in FIG. 17. A nonlimiting example for notification 2 includes "Blue STICKRx: 2 pills now! Take Now!"

In step 303, the dose-app 18 establishes connection to the MDC 16*a* and sends a request to the MDC 16*a* for motion data. The dose-app 18 receives motion data from the MDC 16*a* and the algorithm in the dose-app 18 calculates the likelihood ratio as shown in steps 305 and 306 of FIG. 14.

The algorithm embedded in the dose-app 18 calculates the likelihood ratio in step 305. Based on the motion data received from the MDC, the algorithm determines whether a "valid dose" occurs or whether "no dose" occurs.

When "no dose" is determined (step 307), the dose-app displays a notification 3 on the screen of the mobile device after a set period of time reminding the user to take the dose. Notification 3 is identical to notification 2. If the user does not take the dose after a set time after Notification 3, the dose will result in a "no dose."

When "valid dose" is determined by the algorithm, the dose-app 18 displays a confirmatory screen on the mobile device, (step 309 of FIG. 14). The confirmatory screen at step 309 can be the same as or different from the confirmatory screen 210*a* in FIG. 19. A nonlimiting example of confirmatory screen indicates the name of the medication—in this example, "Hydrochlorothiazide" in a green background (the color green indicating success)—and the message "Good Job!" The "valid dose" is registered in the dose-app 18.

If the user agreed to share her compliance information with one or more third parties, the "valid dose"/"no dose" data (dose event data) is sent to the central server, as shown in step 311. The third party can access the compliance data from the central server to monitor the user's progress.

In another embodiment, the user can open the dose-app 18 and follow the same steps starting at 303.

12. Out-of-Range

In an embodiment, the MDC 16*a* includes a memory chip, such as non-volatile memory chip 34 (as shown in FIG. 2A), for example. Provision of the memory chip enables the tracking of medication dose events that occur when the mobile device 12 is out of range of the MDC 16*a* and memory storage (i.e., when the mobile device is out of the local area). When the user opens the dose-app 18 when back within the in range (i.e., within the local area) of the MDC 16*a*, the dose event data (motion data) stored in the MDC 16*a* is transmitted to the dose-app 18. The algorithm evaluates the stored-motion data from the MDC 16*a* and determines whether or not the stored motion data constitutes a valid dose. The dose-app then logs the stored action as either a "valid dose" or "no dose." When mobile application is set in iBeacon protocol, the MDC will transfer data the next time the application is open, and in the core Bluetooth protocol, whenever it comes back into the local area. This is done by code in the dose-app 18 that is written to search at set times (core Bluetooth) or set actions, such as opening the app (iBeacon).

Figure 15:
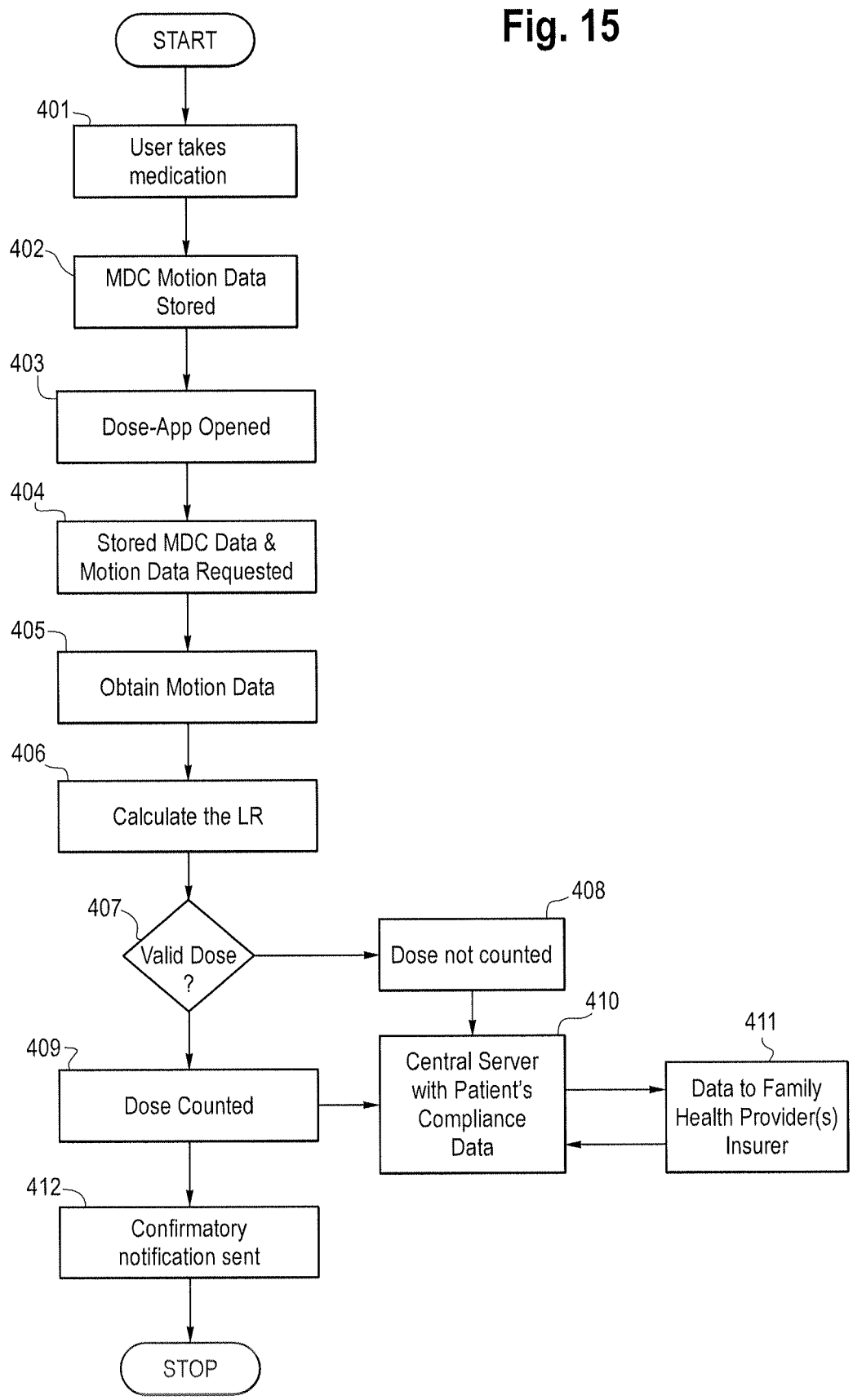
FIG. 15 is a flowchart illustrating a process for managing medication with the dose-app and the motion detection component in accordance with an embodiment of the present disclosure.

FIG. 15 is a flowchart showing a nonlimiting example of operation of system 10 whereby a medication is ingested by a user when the user's mobile device is out of the local area. The user takes medication from a container with an MDC attached thereto. It is understood that the user previously entered medication details in the dose-app (and synchronized the dose-app to the MDC) as previously disclosed herein.

In step 401 in FIG. 15, the user ingests medication from a container having an MDC. The MDC stores the motion data in the memory chip in the MDC (such as non-volatile memory chip 34 in FIG. 3A), as shown in step 402. In step 403, when the user has his/her mobile device and is within the local area, the user opens the dose-app. In the background (transparent to the user), the dose-app requests stored motion data from the MDC 16, as shown in step 404.

In step 405, the MDC transmits the stored motion data to the dose-app. In step 406, the algorithm embedded in the dose-app calculates the likelihood ratio on the stored motion data transmitted from the MDC 16 to the dose-app. Based on the motion data received from the MDC, the algorithm determines whether a "valid dose" occurs (Null hypothesis rejected) or whether "no dose" occurs (Null hypothesis not rejected), step 407. The dose-app registers and stores "valid dose" as a "dose counted" (step 409) or a "no dose" as "dose not counted" (step 408).

If the user agreed to share her compliance information with one or more third parties (family, healthcare provider(s), or insurer), the "valid dose"/"no dose" data (dose event data) is sent to the central server, as shown in step 410. The third party (family, healthcare provider(s), insurer) can access the compliance data from the central server to monitor the user at any time to monitor the user's progress, step 411.

If the algorithm determines the stored motion data from the MDC constituted a "valid dose," the dose-app displays a notification on the mobile device confirming the valid dose, step 412.

In an embodiment, the MDC 16 can be programmed so that the MDC 16 announces its presence to the dose-app only if a "valid dose" is registered. The MDC 16 announcement protocol is changed so the MDC 16 only announces its presence to the dose-app 18 if a "valid dose" is registered. The MDC 16 is programmed to only announce itself if the MDC detects that the medication was taken by the user.

13. Smart Speaker

In an embodiment, the dose-app is embodied in the mobile device and/or embodied in a server. By way of the mobile device and/or the server, the dose-app is operatively connected to a smart speaker. The smart speaker can be in wireless communication with the server and/or the mobile device. A "smart speaker" is a wireless speaker and voice command device with an integrated virtual assistant (artificial intelligence) that offers interactive actions and hands-free activation by way of one or more "hot word(s)." A "hot word" is an audible word (or words) recognized by the smart speaker which initiates the recording of a voice command to the smart speaker. The smart speaker utilizes Wi-Fi, Bluetooth and other wireless protocol standards to perform functions such as audio playback and the control of home automation devices. Nonlimiting examples of smart speakers include Amazon Echo (Alexa intelligent personal assistant) and Google Home (Google Assistant intelligent personal assistant).

With the smart speaker in wireless communication with the dose-app, the smart speaker can be configured to send notifications to the user. When the server (and/or mobile device) indicates that it is time to take a medication to the smart speaker, the smart speaker subsequently transmits an audio notification to the user. The audio notification can be the notification of the text displayed on the mobile device. A user can choose to receive a text notification, audio notification, or both. For example, the dose-app displays on the mobile device, "Time to take blue STICKRx, Hydrochlorothiazide, 1 pill now!" and the smart speaker broadcasts the same notification as an audio notification.

In an embodiment, the user can enter medication information by way of voice command through the smart speaker.

The smart speaker prompts the user with questions to input the medication information in the same way as if the user was entering the medication information on the mobile device. The smart speaker receives the medication information through the user's voice commands; the smart speaker then transmits the medication information to the server which updates itself and the dose-app running on the mobile device.

In an embodiment communication between the mobile device and/or the server and/or the MDC and/or the smart speaker can be performed by use of Gateway connectivity. Gateway connectivity allows for data collection from devices using iBeacon protocol, eddystone, BLE sensors, and other BLE devices without the use of a mobile device or other computing device. Gateway connectivity operates by packaging data it collects and sending the data to a TCP server or remote cloud server by HTTP/MQTT/mbed (ARM) protocol.

In an embodiment, a Gateway device is plugged into an outlet near the MDC's. The Gateway device streams all the data towards the server running the dose-app. When the server and dose-app become aware that a medication is due, both the mobile device and the server will start searching for motion data using sampling. If a valid dose is detected by the mobile device or server via the Gateway device, the dose event is logged and the other device (mobile device or server) is notified. This allows the user to take the medication when the mobile device is outside the local area. The dose-app will still send confirmatory notifications to the mobile device.

In an embodiment, the Gateway device scans for Bluetooth low energy data using a nRF52832 BLE SoC (hereafter referred to interchangeably as "the chip"). The chip performs BLE packet parsing and queening for WiFi transmission. The chip performs WiFi driver implementation based on SPI protocol. The Gateway device is a Texas Instruments SimpleLink CC3100 WiFi Network Processor ("CC3100") for WiFi Connectivity and includes handed data from SPI protocol, and sends the data to the server using TCP protocol. The CC3100 has a simple RBG LED for device status/power, is lined-powered, has a push button for rest, has push button to force device to AP mode (so it can search from one to another WLAN). The chip scans for the Beacon data. When the chip finds Beacon data, the CC3100 packages the data, and sends the data to the CC3100 via SPI protocol which then sends the data to the server via TCP protocol.

It is specifically intended that the present disclosure not be limited to the embodiments and illustrations contained herein, but include modified forms of those embodiments including portions of the embodiments and combinations of elements of different embodiments as come within the scope of the following claims.

The invention claimed is:

1. A system for medication management comprising:
a mobile device comprising a dose software application (dose-app) configured to notify a user to take a medication from a medication container;
a motion detection component attached to the medication container, the motion detection component comprising a motion detection device configured to detect container motion data and wirelessly transmit the motion data to the mobile device;
the mobile device comprising a wireless receiver configured to receive the motion data from the motion detection device and send the motion data to the dose-app, the dose-app configured to:
determine a first probability that the received motion data corresponds to a first motion profile for a no dose event;
determine a second probability that the received motion data corresponds to a second motion profile for proper dispensement of the medication;
determine that the received motion profile corresponds to a valid dose based on the first probability and the second probability, wherein the received motion profile is determined to correspond to a valid dose when the second probability is greater than the first probability or when a ratio of the first probability to the second probability is less than a threshold value,
wherein the second motion profile for proper dispensement of the medication is one of a plurality of motion profiles each corresponding to a type of medication container, and the second motion profile for proper dispensement of the medication corresponds to the type of the medication container.

2. The system of claim 1 wherein the motion detection component comprises a wireless communication component in communication with the motion detection component.

3. The system of claim 2 wherein the motion detection device is a three-axis accelerometer.

4. The system of claim 3 wherein the motion detection component comprises a memory chip.

5. The system of claim 4 wherein the motion detection component is releasably attached to the medication container.

6. The system of claim 1 wherein the dose-app comprises a user interface; and
the dose-app is embodied in instructions stored by the mobile device that, when executed by the mobile device, the dose-app is configured to:
(i) receive user input for medication information.

7. The system of claim 6 wherein the dose-app is embodied in instructions stored by the mobile device that, when executed by the mobile device, the dose-app is configured to:
(ii) synchronize with the motion detection component;
(iii) send a notification for the user to take a medication from the medication container;
(iv) receive motion data from the motion detection device; and
(v) determine whether the motion data constitutes a valid medication dose.

8. The system of claim 7 wherein the dose-app is embodied in instructions stored by the mobile device that, when executed by the mobile device, the dose-app is configured to:
(vi) deactivate the notification; and
(vii) record a dose event.

9. The system of claim 8 wherein the dose-app is embodied in instructions stored by the mobile device that, when executed by the mobile device, the dose-app is configured to:
(viii) display the dose event on the mobile device.

10. The system of claim 9 wherein the dose-app is configured to transmit the dose event to another computing device.

11. The system of claim 1, wherein the second motion profile for proper dispensement of the medication comprising a waveform over a period of time in three-dimensional axes.

12. The system of claim 1, wherein the first motion profile for a no dose event comprising a waveform representing a no dose event created from pre-recorded motion data of the no dose event.

13. A process for managing medication comprising:

synchronizing a motion detection component with a dose software application (dose-app) on a mobile device, the motion detection component attached to a medication container;

the dose-app embodied in instructions stored by the mobile device that, when executed by the mobile device, the dose-app is configured to;

send a notification to a user to take a medication from the medication container;

wirelessly receive motion data from the motion detection component; and determine a first probability that the received motion data corresponds to a first motion profile for a no-dose event;

determine a second probability that the received motion data corresponds to a second motion profile for a no close event;

determine that the received motion profile corresponds to a valid dose based on the first probability and the second probability, wherein the received motion profile is determined to correspond to a valid dose when the second probability is greater than the first probability or when a ratio of the first probability to the second probability is less than a threshold value, wherein the second motion profile for proper dispensement of the medication is one of a plurality of motion profiles each corresponding to a type of medication container, and the second motion profile for proper dispensement of the medication corresponds to the type of the medication container.

14. The process of claim 13 wherein the dose-app has a user interface, the process comprising receiving, by the dose-app, user input for medication information.

15. The process of claim 13 wherein the motion detection component comprises a motion detection device, the process comprising transmitting, with the motion detection device, motion data of the medication container to the dose-app.

16. The process of claim 15 comprising deactivating, with the dose-app, the notification; and recording, with the dose-app, a dose event.

17. The process of claim 16 comprising displaying the dose event on the mobile device.

18. The process of claim 16 comprising transmitting, with the dose-app, the dose event to another computing device.

19. The system of claim 13, wherein the second motion profile for proper dispensement of the medication comprising a waveform over a period of time in three-dimensional axes.

20. The process of claim 13, wherein the first motion profile for a no dose event comprising a waveform representing a no dose event created from pre-recorded motion data of the no dose event.

\* \* \* \* \*